US007807636B1

(12) United States Patent
Darien

(10) Patent No.: US 7,807,636 B1
(45) Date of Patent: Oct. 5, 2010

(54) BOVINE P-SELECTIN GLYCORPOTEIN LIGAND-1

(75) Inventor: Benjamin J. Darien, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 121 days.

(21) Appl. No.: 11/512,934

(22) Filed: Aug. 30, 2006

Related U.S. Application Data

(63) Continuation-in-part of application No. 10/987,751, filed on Nov. 12, 2004, now Pat. No. 7,459,523.

(60) Provisional application No. 60/712,498, filed on Aug. 30, 2005.

(51) Int. Cl.
*A61K 38/00* (2006.01)
*A61K 38/16* (2006.01)
*C12P 21/06* (2006.01)
*C07K 14/00* (2006.01)
*C07K 16/00* (2006.01)

(52) U.S. Cl. ......................... 514/8; 435/69.1; 435/69.7; 514/2; 530/350; 530/387.1; 530/387.7

(58) Field of Classification Search ....................... None
See application file for complete search history.

(56) References Cited

U.S. PATENT DOCUMENTS

| | | | | |
|---|---|---|---|---|
| 5,827,817 | A | 10/1998 | Larsen et al. | |
| 5,840,679 | A | 11/1998 | Larsen et al. | |
| 6,787,365 | B2 | 9/2004 | Varki et al. | |
| 6,852,497 | B2 | 2/2005 | Lorenz et al. | |
| 2002/0031508 | A1* | 3/2002 | Wagner et al. | 424/94.63 |
| 2003/0166521 | A1 | 9/2003 | Eppihimer et al. | |
| 2004/0002585 | A1 | 1/2004 | Holgerson | |
| 2004/0202665 | A1 | 10/2004 | Lazarovits et al. | |
| 2005/0130206 | A1 | 6/2005 | Darien | |

FOREIGN PATENT DOCUMENTS

WO WO09808949 * 3/1998

OTHER PUBLICATIONS

Xu et al., 2006, Veterinary Immunology and Immunopathology, vol. 110, pp. 155-161.*

Strubel et al., 1993, Biochemical and Biosphysical Research Communication, vol. 192, No. 2, pp. 338-344.*

Fritz et al. Force-mediated kinetics of single P-selectin/ligand complexes observed by atomic force microscopy, PNAS, 1998, vol. 95, pp. 12283-12288.*

Burch et al. The N-terminal peptide of PSGL-1 can mediate adhesion to trauma-activated endothelium via P-selectin in vivo. Blood, 2002, vol. 100, issue 2, pp. 531-538.*

Ainsworth; Recurrent airway obstruction (RAO) in horses is characterized by IFN-γ and IL-8 production in bronchoalveolar lavage cells; *Veterinary Immunology and Immunopathology* 96 (2003) 83-91; Ithaca, NY.

Bannerman; *Escherichia coli* and *Staphylococcus aureus* Elicit Differential Innate Immune Responses following Intramammary Infection; *Clinical and Diagnostic Laboratory Immunology*; May 2004; p. 463-472.

Bundgaard; New Consensus Features for Tyrosine *O*-Sulfation Determined by Mutational Analysis; *The Journal of Biological Chemistry*; vol. 272, No. 35, Aug. 29, 1997; pp. 21700-21705.

Carden; Pathophysiology of ischaemia-reperfusion injury; Review Article; Departments of Medicine and Molecular and Cellular Physiology; Louisiana State University Health Sciences Center; Shreveport, LA; John Wiley & Sons, Ltd.; 2000.

Darien; Ischemia/Reperfusion Injury of the Ascending Colon in Ponies: Acorrelative Study Utilizing Microvascular Histopathology and Corrosion Casting; *Scanning Microscopy*; vol. 7, No. 4; 1993; pp. 1311-1320.

Darien; Morphologic Changes of the Ascending Colon during Experimental Ischemia and Reperfusion in Ponies; *Vet Pathol* 32:280-288; 1995.

Elder; Correlation of enterohemorrhagic *Escherichia coli* O157 prevalence in feces, hides, and carcasses of beef cattle during processing; *Proceedings of the National Academy of Sciences of the United States of America*; 2000.

Eppihimer; Heterogeneity of Expression of E- and P-Selectins in Vivo; *Circulation Research.* 1996; 79:560-569; American Heart Association, Inc.

Falati; Accumulation of Tissue Factor into Developing Thrombi In Vivo is Dependent upon Microparticle P-Selectin Glycoprotein Ligand 1 and Platelet P-Selectin; *J. Exp. Med.*; © The Rockefeller University Press; vol. 197, No. 11; Jun. 2, 2003; 1585-1598.

Hansen; NetOglyc: Prediction of mucin type O-glycosylation sites based on sequence context and surface accessibility; *Glycoconjugate Journal* (1998) 15: 115-130.

Hicks; Recombinant P-selectin glycoprotein ligand-1 directly inhibits leukocyte rolling by all 3 selectins in vivo: complete inhibition of rolling is not required for anti-inflammatory effect; *Blood*; Apr. 15, 2003; vol. 101, No. 8; The American Society of Hematoloty; 2003.

Jutila; Cell Surface P- and E-Selectin Support Shear-Dependent Rolling of Bovine γ/δ T Cells; *The Journal of Immunology*; 153: 3917; The American Association of Immunologists; 1994.

Jutila; Analysis of Bovine γδ T Cell Interactions with E-, P-, and L-Selectin; *The Journal of Imunology*; 156; 289-296; The American Association of Immunologists; 1996.

(Continued)

*Primary Examiner*—Robert Landsman
*Assistant Examiner*—Ian Dang
(74) *Attorney, Agent, or Firm*—Charles S. Sara, Esq.; Daniel A. Blasiole; DeWitt Ross & Stevens S.C.

(57) ABSTRACT

A novel bovine P-selectin glycoprotein ligand-1 (bPSGL-1) is disclosed having the amino acid sequence set forth in SEQ. ID. NO:1. DNA sequences encoding the bPSGL-1 are also disclosed, along with vectors, host cells, and methods of using the bPSGL-1. The invention further provides methods for preventing or reducing acute inflammatory response in a bovine subject by administering bPSGL-1 and fragments thereof (e.g., a bPSGL-1 Ig fusion protein). The invention also provides methods for identifying compounds of reducing or preventing damage to tissue or organs caused by acute inflammatory response in a bovine.

13 Claims, 8 Drawing Sheets

OTHER PUBLICATIONS

Karima; The molecular pathogenesis of endotoxic shock and organ failure; *Molecular Medicine Today*; Mar. 1999; pp. 123-132.
Kuckleburg; Bovine platelets activated by *Haemophilus somnus* and its LOS induce apoptosis in bovine endothelial cells; *Microbial Pathogenesis* 38 (2005) 23-32.
Lalko; Equine platelet CD62P (P-selectin) expression: a phenotypic and morphologic study; Veterinary Immunology and Immunopathology; 91 (2003) 119-134.
Lefer; Pharmacology of Selectin Inhibitors in Ishchemia/Reperfusion States; *Annu. Rev. Pharmacol. Toxicol.* 2000; 40:283-94.
Li; Visualization of P-selectin Glycoprotein Ligand-1 as a Highly Extended Molecule and Mapping of Protein Epitopes for Monoclonal Antibodies; *The Journal of Biological Chemistry*; The American Society for Biochemistry and Molecular Biology, Inc.; vol. 271, No. 11; Mar. 15, 1996; pp. 6342-6348; USA.
Ma; P-selectin binding to P-selctin glycoprotein ligand-1 induces an intermediate state of αMβ2 activation and acts cooperatively with extracellular stimuli to support maximal adhesion of human neutrophils; *Blood*; Oct. 15, 2004; vol. 104, No. 8; The American Society of Hematology; 2004.
Middleton; Leukocyte extravasation: chemokine transport and presentation by the endothelium; *Blood*; Dec. 1, 2002; vol. 100, No. 12; pp. 3853-3860; The American Society of Hematology; 2002.
Moore; P-Selectin Glycoprotein Ligand-1 Mediates Rolling of Human Neutrophils on P-Selectin; *The Journal of Cell Biology*; vol. 128, No. 4; Feb. 1995; 661-671; © The Rockefeller University Press.
Moore; Structure and Function of P-Selectin Glycoprotein Ligand-1; *Leukemia and Lymphoma*; vol. 29, pp. 1-15; © Overseas Publishers Accociation; Amsterdam, Netherlands.
Morris; Endotoxemia in Horses: A Review of Cellular and Humoral Mediators Involved in its Pathogenesis; *Journal of Veterinary Internal Medicine*; 1991; 5:167-181.
Myers; New and Effective Treatment of Experimentally Induced Venous Thrombosis with Anti-inflammatory rPSGL-Ig; *Thromb Haemost*; 87:374-82; ©2002 Schattauer GmbH, Stuttgart.
Nguyen; A role for sialyl Lewis-X/A glycoconjugates in capillary morphogenesis; *Nature*; vol. 365; Sep. 16, 1993; © 1993 Nature Publishing Group.
Olson; Chemokines and chemokine receptors in leukocyte trafficking; *Am J Physiol Regulatory Integrative Comp Physiol* 283; R7-R28; © 2002 The American Physiological Society.
Paltrinieri; Bovine Doppel (Dpl) and Prion Protein (PrP) Expression on Lymphoid Tissue and Circulating Leukocytes; *Journal of Histochemistry & Cytochemistry*; vol. 52(12): 1639-1645; 2004; Italy.
Roldán; Soluble E-selectin in cardiovascular disease and its risk factors; *Thromb Haemost* 2003; 90:1007-20; © 2003 Schattauer GmbH, Stuttgart.
Sako; Expression Cloning of a Functional Glycoprotein Ligand for P-Selectin; *Cell*, vol. 75, 1179-1186, Dec. 17, 1993; © Cell Press 1993.
Smalley; L-selectin: mechanisms and physiological significance of ectodomain cleavage; Journal of Cellular and Molecular Medicine; vol. 9, No. 2, pp. 255-266; 2005; Virginia, USA.
Strubel; Isolation and Characterization of a Bovine cDNA Encoding a Functional Homolog of Human P-Selectin; *Biochemical and Biophysical Research Communications*; vol. 192, No. 2, 1993; pp. 338-344; © Academic Press.
Tapper; Modulation of hemostatic mechanisms in bacterial infectious diseases; *Blood*; vol. 96, No. 7, pp. 2329-2337; Oct. 1, 2000.
Vandendries; Role of P-selectin and PSGL-I in coagulation and thrombosis; Pre-published online Aug. 3, 2004; © 2004 Schattauer GmbH, Stuttgart.
Wagner; Horse cytokine/IgG fusion proteins—mammalian expression of biologically active cytokines and a system to verify antibody specificity to equine cytokines; *Veterinary Immunology and Immunopathology*, vol. 105, pp. 1-14; 2005.
Walcheck; Characterization of the bovine peripheral lymph node homing receptor: a lectin cell adhesion molecule (LECAM); *Eur. J. Immunol.* 1992; vol. 22, pp. 469-476.
Weiss; The Sepsis-Coagulant Axis: A Review; *J. Vet. Intern. Med.* 1998; vol. 12, pp. 317-324; © American College of Veterinary Internal Medicine; Minnesota, USA.
Welch; Disseminated Intravascular Coagulation Associated with Colic in 23 Horses (1984-1989); *Journal of Veterinary Internal Medicine*; vol. 6, pp. 29-35.
Wilkins; Structures of the *O*-Glycans on P-selectin Glycoprotein Ligand-1 from HL-60 Cells; *The Journal of Biological Chemistry*; vol. 271, No. 31, pp. 18732-18742; 1996; USA.
Xia; N-terminal residues in murine P-selectin glycoprotein ligand-1 required for binding to murine P-selctin; *Blood*, vol. 101, No. 2, pp. 552-559; © 2003The American Society of Hematology.
Xu; Identification of equine P-selectin glycoprotein ligand-1 (CD162); Springer Science+Business Media, Inc.; vol. 16, pp. 66-71; 2005.
Yang; Mouse P-Selectin Glycoprotein Ligand-1: Molecular Cloning, Chromosomal Localization, and Expression of a Functional P-Selectin Receptor; *Blood*, vol. 87, No. 10, pp. 4176-4186; 1996.

* cited by examiner

ACGCGGGAAGCAGTGGTATCAACGCAGAGTACgCGGGGAGCACAGGCTGAGTCCTTGTCG 60

CTAAAGCAGAGGAACCACTTCTCCTGGGCCCACGAGGTGGCTGTCCCATGGTCTGCTGAG 120

CACGGTGCC 129

*atgtttctgcaactcctgctgcttctggccctgctgggccctggcagcagccac*cagctg 189

M F L Q L L L L L A L L G P G S S H Q L 20 ggggagaccagcacgaatgaaactgtgaaggccccaggcccctatacccaggtgaggag 249

G E T S I N E I V K A P G P L Y P G E E 40 agagacccagaagacgatgaagactatgactatataggacaaacggaccctccagagatg 309

R D P E D D E D Y D Y I G Q I D P P E M 60 cttgacaatatcactgaggtccccaagtttctgcctatggtgacaacgctggggcagaga 369

L D N I T E V P K F L P M V T T L G Q R 80 gagtctgcagggcctatgattcctgagtcattcattctggaggtgtccacaaggactct 429

E S A G P M I P E S F I L E V S T R D S 100 gctgtcctgagtgccacaggggcaaccaccaaaaaactgagtccaaaactggtcacaccg 489

A V L S A T G A T T K K L S P K L V T P 120 gtcccgctgaccaaagaactggttactgaaatccctcccaaagtgaaggatccatccaca 549

V P L T K E L V T E I P P K V K D P S T 140 gagctggctgcggccacagaggccctgtccacagaccccgtgaccacagaggccctgtcc 609

E L A A A T E A L S T D P V T T E A L S 160 acggaacccaggcttacagaagccctgtccacagaacccgtggccacagaggtcctgtcc 669

T E P R L T E A L S T E P V A T E V L S 180 acggaacccaggcttacagaagccctgtccacagaacctgcagccacagaggccctgtcc 729

T E P R L T E A L S T E P A A T E A L S 200 acggaacccaggcttacagaggccctgtccacagaacccaggcttacagaagccctgtcc 789

T E P R L T E A L S T E P R L T E A L S 220 acggaacccgcagccacagagtccctgtccacagaacccaaaatcacagagactctgccc 849

T E P A A T E S L D T E P K I T E T L P 240 acggaaccggccaccacagaagcccctttcagggagcccactaccataccagccctgccc 909

T E P A T T E A P F R E P T T I P A L P 260 acagatccaaccactgtggaggccctgcccacgagaactgctaccacaaggggcctaacc 969

T D P T T V E A L P T R T A T T R G L T 280 acagcccttcctgtggcctctgatactcccaagggcaccactgtggcagctggcaacttg 1029

T A L P V A S D T P K G T T V A A G N L 300 tctgatgacttcactgggaacaaagatcatagcctttttccctggagctctgtggcccca 1089

S D D F T G N K D H S L F P W S S V A P 320 ctccccgcagacggcctgccagacccgggccccgtgaagcagtgtttgctggccatcctc 1149

L P A D G L P D P G P V K Q C L L A I L 340 atcctggccctgctggccaccatcttcctcgtgtgcactgtggtgctggccatccgcctc 1209

I L A L L A T I F L V C T V V L A I R L 360 tcccgcaaggaccacctgtaccccgtgcgcgattactcccccagcgagatggtctgcatc 1269

S R K D H L Y P V R D Y S P S E M V C I 380 tcatctctgctgcccgagcggggcgagggcctgcgcccgtgcccaacggggacctgccc 1329

S S L L P E R G E G P A P V P N G D L P 400 aaggccagggaacagggccggaaggcggggccgagggagggccgtgaaggggatgacctc 1389

K A R E Q G R K A G P R E G R E G D D L 420 accctgcacagcttcctcccttag... 1413

T L H S F L P (SEQ. ID. NO: 2) 427

FIG. 1 (continued on next sheet)

```
CTCCCGAGCTGCTGAGCCAAGGCCCATGCCGAGGCTCTAAGCCCTGGGTCAGGCTGCCTT    1473
GGATCCCCCTGGAGACGGGAATCTTCAGGGCGGGGACCCGGGCTGCCACACACAAGACTG    1533
AGAGCAGCCAGGCTCCAGGCACTGAAGCAGGCCTGGCAAACAGAACCTCCGGTAGAGGCT    1593
GCAGACGACCCCCCAGCTCCCTGCCCAGCCCCCGTGTGTCCTGGGCTCCCTCTAATGCCT    1653
CCGTTCCCTGGCCACTGGAGTCTCATCCTCACGCACCCAGGAGGACTCAGAGTTCGTCCC    1713
TGCTGCCATGCCCGCTACCGTTTCCTTCTACGGTCACTGCACAGGGAGGGGGCACTCTGA    1773
ACTGCATTCCTTAGTTCACTTTCTATCACCCCCCGCTCCTCATTTGGGCTATCTCTCAGG    1833
GAACCCACGGTGAGTTGTGGGGGCTGAGTAGGTTCCTTAGGGGACTCTGTGGACCTACAA    1893
GCTATTGTCTAGTGCCAGCCTAATCCCATCCTGCCCTCCCTCGCCTCCCCCCCCGGGGCC    1953
TTGATTGAGGTGCTCGCAGAGGTCTCCCGCCACCCAGCTCAGGGCCCAGGACGACACACA    2013
CACACACACACACACACACACACGTCGCTCAGTCATGTCCGACTCTCTGCGACCCCATGA    2073
CGGTCAGTAAATGTTTTGGTGGTGATCAAAAAAAA (SEQ. ID. NO: 1)            2108
```

FIG. 1 (continuation)

| | | |
|---|---|---|
| e | MPLPLLLLSLLGPGSRLQL--------VRGQTGVSKYLHRDDV-NRE--GTDLLKTPES | 49 |
| b | MFLQLLLLLALLGPGSSHQLGETSTNETVKAPGPLYPGEERDPE-DDE--DYDYIGQTDP | 57 |
| h | MPLQLLLLLILLGPGNSLQLWDTWADEAEKALGPLLARDRRQAT-EYEYLDYDFLPETEP | 59 |
| m | MSPSFLVLLTILGPGNSLQLQDPWGHETKEAPGPVHLRERRQVVGDDDFEDPDYTYNTDP | 60 |
| | | |
| e | S--TKTFS---LSPRLLDVMGTPEQRDSTGPGTPEPATLEVAMEDSAGLGAGGTAVGNLT | 104 |
| b | PEMLDNIT---EVPKFLPMVTTLGQRESAGPMIPESFILEVSSTRDSAVLSATGATTKKLS | 114 |
| h | PEMNRLST---DTTPLT------------GPGTPESTTVEPAARRSTGLDAGGAVT-ELT | 103 |
| m | PELLKNVTNTVAAHPELPTTVVMLERDSTSAGTSERATEKIATTDPTAPGTGGTAVGMLS | 120 |
| | | |
| e | TELATQGISVTMGPLTEGLVTTNPPFLEALSTDGAQSTELDTLEALSTGPAATEALTTQP | 164 |
| b | PKLVTP------VPLIKELVTEIPPKVKDPSTELAAAT-----EALSTDPVTTEALSTEP | 163 |
| h | TELANMG-NLSTDSAAMEIQTTQPAATEAQTTPLAATE------AQTTRLTATEAQTTPL | 156 |
| m | TDSATQW-------SLTSVETVQPASTEVETSQPTPME------ADTSKPAPMEAETSQP | 167 |
| | | |
| e | AATEVLSTEPAATEALTTQPAATEVLSTEPAATEALTTQPAATEVLSTEPAATEALTSQP | 224 |
| b | RLTEALSTEPVATEVLSTEPRLTEALSTEPAATEALSTEPRLTEALSTEPRLTEALSTEP | 223 |
| h | AATEAQTTPPAATEAQTTQPTGLEAQTTAPAAMEAQTTAPAAMEAQTTPPAAMEAQTTQT | 216 |
| m | APMEAETSQPAPMEAETSQPAPMEAETSQPAPNEAETSKPAPTEAETSKPAPTEAETTQL | 227 |
| | | |
| e | AATEVLSKGPAATEALTTQPAATEVLSTEPAATEALTSQPAATEVLSKGPAATEALTTQP | 284 |
| b | AATESLSTEPKITETLPTEPATTEAPFREPTTIPALPTDPTTVEALPTRTATTRGLTTAL | 283 |
| h | TAMEAQTTAPEATEAQTTQPTATEAQTIPLAAMEALSTEPSATEALSMEPTTKRGLFIPF | 276 |
| m | PRIQAVKT-------LFTTSAATEVPSTEPTTMETASTE-------SNESTIFLGPSVTH | 273 |
| | | |
| e | AVTEAQ---STVLA---TTSFRG-KSQTVSLLSSTVPNPTVAW-DHIPVKQCLLAILILA | 336 |
| b | PVASDTPKGTTVAAGNLSDDFTGNKDHSLFPWSSVAPLPADGLPDPGPVKQCLLAILILA | 343 |
| h | SVSSVTHKGIPMAA------------------SNLSVNYPVGAPDHISVKQCLLAILILA | 318 |
| m | LPDSGLKKGLIVTP------------------GSSPAPTLPGSSDLIPVKQCLLIILILA | 315 |
| | | |
| e | LLATIFLVCTVVLAVRLSRKNHTYPVRSYSPTEMVCISSLLPEGGEGPTTTANGGLPTPK | 396 |
| b | LLATIFLVCTVVLAIRLSRKDHLYPVRDSPSEMVCISSLLPERGEGPAPVPNGDLPKAR | 403 |
| h | LVATIFFVCTVVLAVRLSRKGHMYPVRNYSPTEMVCISSLLPDGGEGPSATANGGLSKAK | 378 |
| m | SLATIFLVCTVVLAVRLSRKTHMYPVRNYSPTEMICISSLLPEGGDGAPVTANGGLPKVQ | 375 |
| | | |
| e | GRGRKAGPGEDHDGDDLTLHSFLP **(SEQ. ID. NO: 3)** | 420 |
| b | EQGRKAGPREGREGDDLTLHSFLP **(SEQ. ID. NO: 4)** | 427 |
| h | SPGLTPEPREDREGDDLTLHSFLP **(SEQ. ID. NO: 5)** | 402 |
| m | D--LKTEPSGDRDGDDLTLHSFLP **(SEQ. ID. NO: 6)** | 397 |

FIG. 2A

| | Signal Peptide | Propeptide | P-selectin binding domain | Decameric repeats | Cys | TM domain (23aa) | Cytoplasmic domain (67-69aa) |
|---|---|---|---|---|---|---|---|
| Human | 1-18 | 38-41 | 42-57(16) | 118-267(15) | Cys310 | 311-333 | 334-402 |
| Mouse | 1-18 | 38-41 | 42-58(17) | 133-232(1) | Cys307 | 308-330 | 331-397 |
| Bovine | 1-18 | N/A | 19-55(37) | 145-244(10) | Cys335 | 336-358 | 359-427 |
| Equine | 1-18 | N/A | 19-49(31) | 151-290(14) | Cys328 | 329-351 | 352-420 |
| Amino acid identity | | | | | | | |
| Bovine/Human | 77% | N/A | 25% | 48% | - | 86% | 71% |
| Bovine/Equine | 72% | | 12% | 68% | | 95% | 72% |
| Bovine/Murine | 44% | | 29% | 29% | | 86% | 65% |

FIG. 2B

Equine:
19 QLVRGQTGVSKYLHRDDVNREGTDLLKTPES 49 (SEQ. ID. NO: 16)

Bovine:
19 QLGETSTNETVKAPGPLYPGEERDPEDDEDYDYIGQTDPPEM 60 (SEQ. ID. NO: 17)

Human:
42 QATEYEYLDYDFLPETEPPEM 62 (SEQ. ID. NO: 18)

Mouse:
42 QVVGDDDFEDPDYTYNTDPPEM 63 (SEQ. ID. NO: 19)

BOVINE P-SELECTIN GLYCORPOTEIN LIGAND-1

CROSS-REFERENCE TO RELATED APPLICATIONS

Priority is hereby claimed to provisional application Ser. No. 60/712,498, filed Aug. 30, 2005, which is incorporated herein by reference. This application is also a continuation-in-part of application Ser. No. 10/987,751, filed Nov. 12, 2004 now U.S. Pat. No. 7,459,523, which is incorporated herein by reference.

FIELD OF THE INVENTION

This invention is directed to the field of veterinary medicine. More particularly, the present invention is directed to a novel bovine P-selectin glycoprotein ligand-1 (bPSGL-1), isolated nucleotides encoding the same, and therapeutic methods directed to targeting leukocyte-mediated inflammation and bovine neonatal septicemia and enteritis with a natural bovine-specific P-selectin glycoprotein ligand-1 immunoglobulin (bPSGL1-Ig) chimera.

CITED REFERENCES

Full citations of the references cited in this document can be found in the BIBLIOGRAPHY preceding the claims.

BACKGROUND OF THE INVENTION

Despite recent progress, mortality remains high in cows with severe abdominal crises, such as intestinal ischemia, salmonellosis, and neonatal septicemia (Morris 1991; Welch et al. 1992). Nationwide, pre-weaning heifer mortality rates approach 10%, with the majority of deaths attributed to diarrhea and systemic infection. In these acute inflammatory diseases, the inflammatory reaction is triggered with cytokines and the release of inflammatory mediators, with platelets activated either by endotoxins released from gram-negative bacteria and/or the coagulation cascade (Weiss and Rashid 1998). The inflammatory reaction can result in vascular injury and possibly thrombosis, which is the final and often fatal outcome of these disorders.

The inflammatory reaction begins with the tethering and rolling of the circulating leukocytes on an activated endothelium (McEver and Cummings 1997). The rolling process is mediated by the selectins, a family of $Ca^{2+}$-dependent proteins. Membrane-bound selectins are expressed on the surface of endothelial cells (E-selectin), leukocytes (L-selectin), and platelets (P-selectin). All selectins contain a C-type carbohydrate recognition domain at their N-terminus which plays a crucial role in interacting with their ligand proteins.

P-selectin glycoprotein ligand-1 (PSGL-1) is a dimeric, mucin-like glycoprotein constitutively expressed on leukocyte surfaces which binds to P-, E- and L-selectin. In humans, P-selectin/PSGL-1 binding plays a central role in inflammatory and thrombotic mechanisms in ischemic conditions by regulating leukocyte trafficking through cell adhesion, platelet-leukocyte aggregate formation and tissue factor expression. For instance, human P-selectin mediates leukocyte adhesion via its natural ligand, P-selectin glycoprotein ligand-1 (hPSGL-1). hPSGL-1 is located on the surface of a variety of leukocytes, including neutrophils, monocytes, eosinophils, and lymphocytes (Hicks et al. 2002). Human disorders associated with PSGL-1 binding share comparable pathomorphological features with common disorders in cattle, including enteritis, mastitis, and *Haemophilus somnus* infection, which can cause pneumonia, abortion, arthritis, septicemia, myocarditis and thromboembolic meningoencephalitis (TME). Due to the high basal state of platelet P-selectin expression, cows are likely predisposed to inflammatory and thrombotic disorders during gram-negative septicemia and endotoxemia as a result of enhanced platelet-leukocyte interaction via bovine PSGL-1 (bPSGL-1).

Treatments for these diseases in cattle include the use of antibiotics to treat the bacterial infection causing the inflammatory reaction and non-steroidal anti-inflammatory drugs (NSAIDs) to treat inflammatory symptoms. However, the use of antibiotics in food animals selects for resistant pathogens and resistance genes that may be transferred to humans through the consumption or handling of foods of animal origin. Recent studies have demonstrated that antimicrobial-resistance among food-borne bacteria may cause excess cases of illness, prolonged duration of illness, and increased rates of bacteremia, hospitalization, and death in humans. The continued availability of safe and effective antimicrobials for humans and animals depends upon the responsible use of these products.

Public health concerns related to the use of antibiotics and anti-inflammatory drugs in the dairy industry warrant the development of novel therapeutics that address the medical needs of the dairy industry yet respect these public health concerns. Additionally, the concurrent use of several of these pre-slaughter intervention strategies could synergistically decrease human illnesses by providing for additional barriers in a multiple-hurdle approach to improving food safety. A bovine-specific drug that reduces morbidity and mortality in dairy calves with scours or systemic infection will greatly impact the profit margin of dairy farmers while also reducing the prevalence of antibiotic resistant strains of bacteria entering the food chain and 'illegal' use of NSAIDs in food animals, a positive benefit to the food industry.

It can be appreciated that there exists a need in veterinary medicine for improved methods of treating bovine subjects susceptible to or suffering from acute inflammatory responses including scours and systemic infection. Methods to universally treat and/or prevent such disorders are highly sought after and their discovery would be welcomed by bovine owners and veterinarians alike.

Thus, an objective of the present application is to develop a bovine-specific molecule that targets cell adhesion molecules which regulate early events in leukocyte trafficking. Treatment with this molecule will likely minimize the vascular and organ tissue injury which is commonly associated with intestinal inflammation and septicemia.

SUMMARY OF THE INVENTION

The present invention provides various bovine P-selectin glycoprotein ligand-1 (bPSGL-1) polypeptides based on the amino acid sequence set forth in FIG. 1. Nucleic acids encoding the bPSGL-1 polypeptides are also disclosed (see SEQ. ID. NOS: 1 and 2), along with vectors, host cells, and methods of making bPSGL-1 polypeptides and fusion proteins based thereon. In addition, the invention provides therapeutic methods of reducing or preventing acute inflammatory response by administrating bPSGL-1 polypeptides and related fusion proteins.

In a first embodiment, the present invention provides an isolated polypeptide comprising an amino acid sequence as shown in SEQ. ID. NO: 2, an amino acid sequence at least 85% identical to the amino acid sequence in SEQ. ID. NO: 2, a fragment of the amino acid sequence in SEQ. ID. NO: 2 or a conservative variation thereof capable of binding bovine P-selectin; or an immunogenic fragment comprising at least 10 contiguous amino acid residues of the amino acid sequence set forth in SEQ. ID. NO: 2.

Certain preferred polypeptides according to the invention include at least a portion of the extracellular domain of bPSGL-1 predicted to provide bovine P-selectin binding capacity. Particularly preferred polypeptides include a fragment of amino acid sequence comprising contiguous amino acid residues selected from the extracellular domain of bPSGL-1 or conservative variations thereof capable of binding bovine P-selectin. Such polypeptides or conservative variations thereof may be further modified by sulfation, glycosylation, or both.

In addition, the invention encompasses isolated nucleic acids comprising a nucleotide sequence encoding a bPSGL-1 polypeptide as set forth in SEQ. ID. NO: 2 (for a suitable nucleotide sequence, see SEQ. ID. NO: 1); a nucleotide sequence capable of hybridizing under stringent conditions (such as those conditions described in application Ser. No. 10/987,751) to a nucleotide sequence-specified encoding a bPSGL-1 polypeptide as set forth in SEQ. ID. NO: 2, a nucleotide sequence capable of hybridizing under stringent conditions to a nucleotide sequence encoding a bPSGL-1 polypeptide capable of binding bovine P-selectin; a nucleotide sequence encoding a polypeptide fragment capable of binding bovine P-selectin; a nucleotide sequence complementary to the above-described nucleotide sequences; or an RNA equivalent. A particularly preferred nucleic acid according to the invention includes the open reading frame for bPSGL-1. The present invention is further directed to a host cell transformed with the isolated nucleic acid.

In yet another embodiment, the invention provides pharmaceutical compositions comprising a therapeutically effective amount of a polypeptide including bPSGL-1 amino acid sequence set forth in SEQ. ID. NO: 2 capable of binding bovine P-selectin or a conservative variation thereof, and a pharmaceutically-acceptable carrier. In preferred embodiments, such pharmaceutical compositions comprise the recombinant bPSGL-1-Ig fusion polypeptides described and claimed herein.

In certain embodiments, the invention is directed to recombinant bPSGL-1-Ig fusion proteins comprising an amino acid sequence from the extracellular domain of bPSGL-1 or a conservative variation thereof capable of binding bovine P-selectin, and a heterologous amino acid sequence derived from an immunoglobulin. Recombinant bPSGL-1-Ig polypeptides according to the invention are useful as bovine P-selectin antagonists and consequently effective in preventing or reducing acute inflammatory responses in bovine subjects.

In yet another embodiment, the invention provides a method of inhibiting P-selectin-mediated disease in a subject comprising administering to a subject in need thereof a therapeutically effective amount of a composition comprising a pharmaceutically acceptable carrier and an isolated glycoprotein having bovine P-selectin ligand activity. The acute inflammatory response may, for example, be related to intestinal ischemia, salmonellosis, or septicemia. A preferred bovine P-selectin antagonist is a soluble bPSGL-1 polypeptide capable of binding bovine P-selectin, as described above. In more preferred embodiments, the polypeptide further comprises a heterologous sequence derived from an immunoglobulin where the P-selectin antagonist is a bPSGL-1-Ig fusion protein.

The present invention further provides a method of treating P-selectin-mediated disease such as thrombosis, cell adhesion to blood vessels, leukocyte-mediated inflammation, or variations thereof in a subject comprising administering to a subject in need thereof a therapeutically effective amount of a composition comprising a pharmaceutically acceptable carrier and an isolated glycoprotein having bovine P-selectin ligand activity.

The invention further provides a method of producing an isolated bPSGL-1 polypeptide. The method comprises culturing a host cell containing an isolated nucleic acid encoding a bPSGL-1 polypeptide under conditions that allow expression of the bPSGL-1 polypeptide, and purifying the bPSGL-1 polypeptide from the host cell. In preferred embodiments, the process further includes modifying the bPSGL-1 polypeptide by sulfation, glycosylation, or both.

The present invention is also directed to a method of preventing or reducing an acute inflammatory response in a subject, comprising administering to the subject in need thereof an effective amount of a composition comprising a bovine P-selectin antagonist.

The present invention also provides a method of screening for a compound that modulates the activity of a bPSGL-1 polypeptide. The method comprises combining a bPSGL-1 polypeptide with at least one test compound under conditions permissive for the activity of the polypeptide, assessing the activity of the polypeptide in the presence of the test compound, and comparing the activity of the polypeptide in the presence of the test compound with the activity of the polypeptide in the absence of the test compound, wherein a change in the activity of the polypeptide in the presence of the test compound is indicative of a compound that modulates the activity of the polypeptide.

Finally, the present invention provides a method of producing bPSGL-1-IgG chimeric protein comprising inserting cDNA-encoding bPSGL-1 extracellular domains into an expression vector containing an enterokinase digestion site to define an expression construct, transiently transfecting the expression construct, testing for fusion protein concentration, determining presence and amount of bPSGL-1-IgG secretion, purifying the secretion with a protein G affinity column, and collecting recombinant bPSGL-1 by enterokinase digestion.

In certain embodiments, the method of screening identifies compounds that modulate the direct physical interaction between a bPSGL-1 polypeptide and bovine P-selectin. These methods may include labeling the isolated bPSGL-1 with a fluorescent molecule and monitoring the interaction between bPSGL-1 polypeptide and the bovine P-selectin through monitoring changes in fluorescence intensity, fluorescence polarization, or fluorescence energy resonance transfer. In other embodiments, the method of screening identifies compounds capable of modulating the intracellular signaling activity of bPSGL-1.

Therapeutic molecules for use in humans have been developed by creating chimeras of the human PSGL-1 and immunoglobulin. Similar molecules also have been created using the equine protein for treatment of disease in horse. See application Ser. No. 10/987,751. Based on some similarities between human, equine and bovine PSGL-1 amino acid sequence, it is very likely that therapeutic molecules may be developed using the bovine protein. The invention includes this chimera and use as a therapeutic.

The high therapeutic value of the present invention suggests its usefulness in developing kits to study PSGL-1/P selectin binding. Further, the bovine sequence may likely function as a substitute for human PSGL-1 due to the similarity in modes of action. Therefore, the present invention has relevance as a human therapeutic.

The objects and advantages of the invention will appear more fully from the following detailed description of the preferred embodiment of the invention made in conjunction with the accompanying drawings.

BRIEF DESCRIPTION OF THE DRAWINGS

FIG. 1 illustrates the complete cDNA and encoded amino acid sequence of bPSGL-1 (see SEQ. ID. NOS: 1 and 2, respectively).

FIG. 2A compares the homology of amino acid sequences between equine (e) PSGL-1 (SEQ. ID. NO: 3), bovine (b) PSGL-1 (SEQ. ID. NO: 4), human (h) PSGL-1 (SEQ. ID. NO: 5) and mouse (m) PSGL-1 (SEQ. ID. NO: 6).

FIG. 2B illustrates the alignments of PSGL-1 amino acid identity between equine (e), bovine (b), human (h) and mouse (m).

In FIG. 6A, CHO cells were gated based on typical forward and side scatter physical characteristics. In FIG. 6B, gates were set to the negative control, meaning CHO cells transfected with pcDNAIGHG1 without insert. FIG. 6C shows CHO cells successfully transfected with ePSGL-1-IgG plasmid and expressed ePSGL-1-Ig protein.

DETAILED DESCRIPTION OF THE INVENTION

Figures 3, 4:
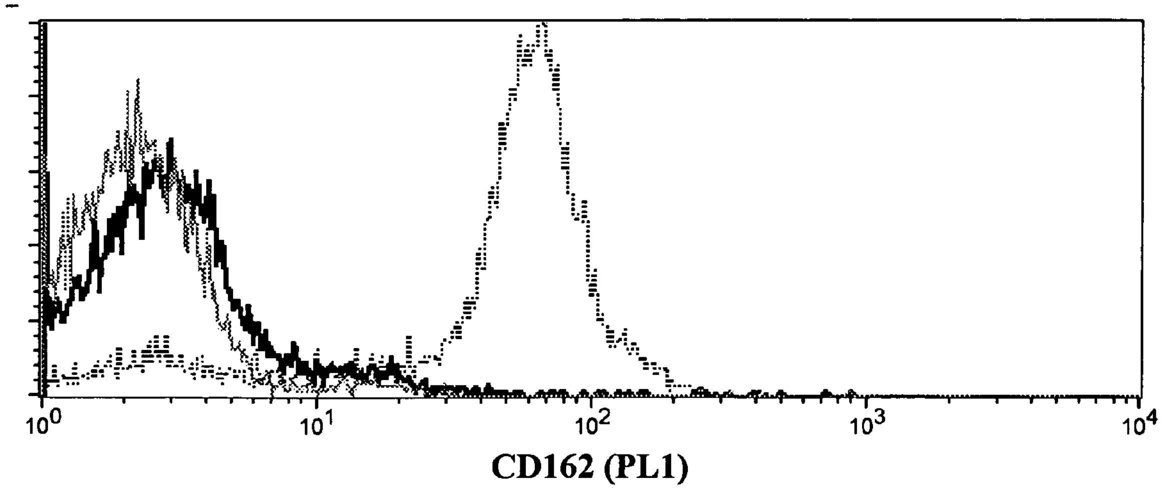
FIG. 3 illustrates the alignments of $NH_2$-terminal amino acid sequences of mature equine (e) PSGL-1 (SEQ. ID. NO: 16), bovine (b) PSGL-1 (SEQ. ID. NO: 17), human (h) PSGL-1 (SEQ. ID. NO: 18), and mouse (m) PSGL-1 (SEQ. ID. NO: 19).
FIG. 4 illustrates the flow cytometric analysis of constitutive expression of CD162 (PL1) on bovine leukocytes.

Unless defined otherwise, all technical and scientific terms used in this document have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention. Reference is particularly made to application Ser. No. 10/987,751, which has already been noted as being incorporated herein by reference. Applicant's application is particularly useful for the definitions of terms, most of which apply equally to this application and to the bovine species. As such, the definitions and descriptions of the various materials and methods will not be duplicated in this document in their entirety.

A "conservative amino acid substitution" is one in which the amino acid residue is replaced with an amino acid residue having a similar side chain. Polypeptides including one or more such conservative substitutions are termed "conservative variations" or "conservative variants" of a respective parent polypeptide. Further, the biological function between parent and conservative variant are substantially conserved. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The present invention provides polypeptides, nucleic acids, compositions and methods for the prevention or reduction of damage caused by acute inflammatory response in a bovine subject. Damage may be directed to a particular tissue or organ, as in intestinal ischemia, or damage may be systemic, as in the septicemia that commonly strikes bovine neonates, i.e., neonatal septicemia. Accordingly, the present invention provides methods of administering a bovine P-selectin antagonist, e.g., a soluble bPSGL-1, or a fragment thereof having bPSGL-1 activity, e.g., a bPSGL-1-Ig fusion protein. The bovine P-selectin antagonist may be administered to a subject in need thereof prior to or during an acute inflammatory response.

The present invention also includes isolated bPSGL-1 proteins, e.g., bPSGL-1 proteins, and biologically active portions thereof, as well as polypeptide fragments suitable for use as immunogens to raise anti-bPSGL-1 antibodies. In one embodiment, native bPSGL-1 proteins can be isolated from cells or tissue sources by an appropriate purification scheme using standard protein purification techniques. In another embodiment, bPSGL-1 proteins are produced by recombinant DNA techniques. Alternative to recombinant expression, a bPSGL-1 protein or polypeptide can be synthesized chemically using standard peptide synthesis techniques. In a preferred embodiment, the bPSGL-1 protein has at least an extracellular domain of the amino acid sequence shown in SEQ. ID. NO: 2 or bovine P-selectin binding fragment of the extracellular domain of bPSGL-1.

Thus, certain bPSGL-1 proteins according to the invention are soluble bPSGL-1 molecules. A DNA encoding a soluble form of the bPSGL-1 may be prepared by expression of a modified DNA in which the regions encoding the transmembrane and cytoplasmic domains of the bPSGL-1 are deleted and/or a stop codon is introduced 3' to the codon for the amino acid at the carboxy terminus of the extracellular domain. The gene encoding PSGL-1 has been cloned.

Research Design/Procedure:

The laboratory techniques and DNA/protein manipulation methods used herein are well known to the art. Reference is made to applicant's application Ser. No. 10/987,751.

The present invention identifies the morphological and functional expression of bPSGL-1 in bovine monocytes and confirms that bovine platelet P-selectin regulates coagulation and inflammation in leukocytes via PSGL-1. Specifically, the present invention:

a) Defines the amino acid residues that control P-selectin and bPSGL-1 receptor binding properties on bovine monocytes. A series of N-terminal deleted bovine PSGL-1 plasmids were constructed and expressed to determine the essential region of PSGL-1 required for efficient P-selectin binding by comparing the P-selectin binding activity with the deleted PSGL-1 and wild-type PSGL-1.

b) Determines the role of bPSGL1-Ig mediated signal transduction and cytokine and tissue factor expression after binding to P-selectin. A K562-P-selectin-CHO—PSGL-1 or K562-P-selectin-monocyte model in vitro will be established to detect the induction of cell signaling, expression of tissue factor and induction of cytokine biosynthesis.

c) Determines if bPSGL1-Ig regulates platelet-monocyte binding, signal transduction, and chemokine and tissue factor expression in monocytes in a P-selectin dependent mechanism. An anti-adhesion chimeric molecule (bPSGL1-Ig chimeric protein) will be utilized to investigate the efficacy of bPSGL1-Ig in regulating P-selectin/PSGL-1 mediated inflammation and coagulation.

Bovine P—Selectin Glycoprotein Ligand-1 (bPSGL-1):

bPSGL-1 cDNA is 2108 base pairs in length, predicting a protein of 427 amino acids with an 18 amino acid signal peptide, an extracellular region with a mucin-like domain, and transmembrane and cytoplasmic domains (see FIG. 1 and SEQ. ID. NO: 1). The amino acid sequence of bPSGL-1 demonstrated 52%, 49% and 40% overall homology to equine, human and mouse, respectively (see FIG. 2A). A single extracellular cysteine, at the transmembrane and extracellular domain junction, suggests a disulfide bonding pattern. Alignment of bovine with equine, human and mouse PSGL-1 demonstrates a high conservation of transmembrane and cytoplasmic domains, but diversity of the extracellular domain (see FIG. 2B). This is especially apparent in the anionic $NH_2$-terminal of PSGL-1, the putative P-selectin binding domain (see FIG. 3). In the $NH_2$-terminal of bPSGL-1, there are three potential tyrosine sulfation sites and three potential threonine O-glycosylation sites. Each of these is required for P-selectin binding in human PSGL-1 (hPSGL-1). Although bPSGL-1 shares 57% homology in amino acid sequence in the corresponding epitope region that binds the monoclonal antibody PL1 for hPSGL-1, no cross reactivity was found in bovine leukocytes. Thus, bPSGL-1 shares homology with hPSGL-1, but has differences in the putative extracellular P-selectin binding domain.

Referring now to FIG. 1 and SEQ. ID. NO: 1, the amino acid sequence of bovine PSGL-1 is compared to equine PSGL-1. The signal peptide sequence is shown in italics, and the mature bPSGL-1 protein begins at amino acid residue 19 of FIG. 1 (residue 1 as shown in SEQ. ID. NO: 1). The residues in putative PSGL-1/P-selectin interaction region, based on the presence of tyrosine and threonine residues (shaded grey and underlined) are in bold. The asparagine residues (single underline in FIG. 1) denote the potential N-linked glycosylation sites. The putative mucin-like domain, including ten decameric repeats, are also underlined. The cysteine residue preceding the transmembrane domain is bolded. The transmembrane domain is double-underlined. The nucleotide sequence of the polyadenylation sites is shaded in grey.

Effective interactions between leukocytes, platelets and endothelia at sites of vascular injury are critical steps in the host inflammatory response (Middleton et al., 2002; Olson and Ley, 2002). P-selectin, E-selectin and L-selectin are a three member family of adhesion proteins that are responsible for many of these interactions (Vandendries et al., 2004; Roldan et al., 2003; Smalley and Ley, 2005) and each selectin has been identified and characterized in cattle (Nguyen et al., 1993; Strubel et al., 1993; Walcheck et al., 1992). Functional roles for these vascular selectins in the bovine have been established for leukocyte binding and rolling at the endothelial surface (Jutila et al., 1994; Jutila and Kurk, 1996). However, there is an absence of literature and detail regarding the natural ligands for these selectins such as bovine P-selectin glycoprotein ligand-1 (bPSGL-1) and the specifics of selectin-ligand interaction. Leukocyte trafficking, vasculitis and thrombosis are common pathomorphologic features of numerous infectious diseases in cattle and further studies into the pathogenesis of diseases such as thromboembolic meningoencephalitis, bacterial pneumonia, and mastitis may benefit from greater knowledge regarding the molecular basis of selectin/ligand interaction.

Prophylactic and Therapeutic Methods According to the Invention. P-selectin has several functions related to vascular injury and thrombosis including mediating rolling of leukocytes on vascular endothelium, promoting interaction of platelets with leukocytes resulting in leukocyte activation and release of tissue factor rich microparticles from these activated cells and or pro-inflammatory mediators the further activate endothelium cells to promote more leukocyte capture; capture of leukocyte derived microparticles on clots and endothelium to promote clot growth; and plugging of microvessels to extend areas of ischemia. Specific inhibitors of P-selectin interaction with its ligand PSGL would be expected to significantly reduce these events. In the case of bovine rPSGL-Ig, this soluble ligand construct would be expected to bind to expressed bovine P-selectin on endothelium and platelets and thus reduce the ability of native bPSGL-1 on the surface of leukocytes or leukocyte derived microparticles to bind. The effect of the presence of bovine rPSGL-Ig would be to reduce inflammatory and thrombotic responses in situations resulting in increased bovine P-selectin/bPSGL-1 interactions.

Inhibition of bovine P-selectin/bPSGL-1 interactions may be particularly useful in thrombotic stroke. Reduction in formation of activated platelet/leukocyte complexes with rPGSL-Ig could improve microvascular flow downstream of the vascular obstruction by reducing vascular plugs due to platelet/leukocyte complexes formed as a result of P-selectin/bPSGL-1 interactions. This improved microvascular flow could reduce infarct growth and thus reduce the extent of long term damage to a tissue or organ. In addition, by reducing leukocyte/endothelial cell rolling, rPSGL-Ig could reduce the extent of reperfusion injury following clot lysis.

Use of rPSGL-Ig may also be beneficial in treating bovine subjects with or susceptible to septicemic disorders. Septicemia is known to cause the release of inflammatory mediators from the activated blood cells. These agents are known to promote expression of P-selectin on platelets and endothelium cells. Reduction of these secondary inflammatory responses by early intervention with a selectin antagonist could prove to be very beneficial in reducing morbidity and mortality associated with septicemic conditions.

In one aspect, the invention provides a method for modulating, e.g., treating, preventing, or reducing organ or tissue damage, e.g., intestinal damage, caused by reperfusion injury following ischemia in an bovine subject by administering to the subject a composition which includes an agent which modulates bPSGL-1 expression or bPSGL-1 activity, e.g., modulates bovine P-selectin binding, modulates cellular adhesion, e.g., cell-to-cell adhesion (e.g., leukocyte-endothelial cell adhesion or leukocyte-platelet adhesion), and cell (e.g., leukocyte) adhesion to blood vessels, and modulates leukocyte rolling. Bovine subjects at risk for ischemia and/or reperfusion injury can be identified by, for example, any or a combination of veterinarian diagnostic or prognostic assays known by one of skill in the art. Administration of a prophylactic or therapeutic agent, e.g., a bPSGL-1 molecule, or a fragment thereof having bovine P-selectin ligand-1 activity, e.g., soluble bPSGL-1, or a soluble recombinant bPSGL-1 fusion protein, e.g., rPSGL-Ig, can occur prior to reperfusion, such that damage to tissue and organs is inhibited or reduced.

Methods of administering to an bovine subject a P-selectin antagonist, e.g., an anti-P-selectin ligand-1 antibody, soluble P-selectin ligand-1, soluble bPSGL-1, or fragments thereof, or soluble rPSGL-Ig, to treating, preventing, or reducing organ or tissue damage following ischemia and/or reperfusion, include, but are not limited to, the methods described in applicant's application Ser. No. 10/987,751 as it applies to the equine species. This includes administration in the form of a pharmaceutical composition suitable for such administration. Such compositions typically include an effective amount of the active agent (e.g., protein or antibody) and a pharmaceutically acceptable carrier. Pharmaceutical compositions suitable for injectable use include sterile aqueous solutions (where water soluble) or dispersions and sterile powders for the extemporaneous preparation of sterile injectable solutions or dispersion. Oral compositions generally include an inert diluent or an edible carrier. They can be enclosed in gelatin capsules or compressed into tablets. For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. The agents that modulate bPSGL-1 activity can also be prepared in the form of suppositories (e.g., with conventional suppository bases such as cocoa butter and other glycerides) or retention enemas for rectal delivery.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the seventy of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to an bovine (e.g., a cow) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a therapeutic agent or a radioactive metal ion. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, Pseudomonas exotoxin, or diphtheria toxin; a protein such as tumor necrosis factor, alpha-interferon, beta-interferon, nerve growth factor, platelet derived growth factor, tissue plasminogen activator; or biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Screening Assays. The invention further provides methods (also referred to herein as "screening assays") for identifying modulators, i.e., candidate or test compounds or agents (e.g., peptides, peptidomimetics, small molecules, ribozymes, or bPSGL-1 antisense molecules) which bind to bPSGL-1 proteins, have a stimulatory or inhibitory effect on bPSGL-1 expression or bPSGL-1 activity, or have a stimulatory or inhibitory effect on the expression or activity of a bPSGL-1 target molecule, e.g. P-selectin, or have an effect, e.g., inhibition of cellular migration or adhesion, on cells expressing a bPSGL-1 target molecule, e.g., endothelial cells and activated platelets. Compounds identified using the assays described herein may be useful in, for example, treating, preventing, or reducing tissue and organ damage due to acute inflammatory response. Reference is made to applicant's application Ser. No. 10/987,751 for details. It is within the scope of those skilled to the art to adapt the condition to the use of the bovine species.

The following experiments were designed to sequence bPSGL-1 and investigate its cross reactivity with human PL1 Ab, the human monoclonal blocking Ab for human PSGL-1 (h-PSGL-1). All experimental procedures were performed in accordance with the guidelines of the University of Wisconsin Institutional Animal Care and Use and Bio-safety Committees.

EXPERIMENTS

Experiment 1

Sequencing bPSGL-1 and Investigating its Cross Reactivity with Human PL1 Ab

Human PL1 Ab is the human monoclonal blocking Ab for h-PSGL-1. Peripheral blood was obtained by jugular venipuncture from healthy Holstein cattle using sodium citrate (0.38% final volume) as an anticoagulant. The whole blood was lysed in a lysing solution as described previously (Paltrinieri et al., 2004), and the leukocytes were collected by centrifuge for 10 min at 250×g. The leukocytes were then washed three times in 1×PBS. Leukocytes were either lysed in TRIZOL reagent (Invitrogen, Carlsbad, Calif.) for RNA isolation or were resuspended in 1×PBS/2% BSA/0.01% sodium azide solution, fixed in paraformaldehyde (PFA) (1% final concentration) for 30 minutes at 4° C. and washed using PBS/BSA for later PL1 staining and FACS analysis.

To identify bPSGL-1 cDNA, an equine PSGL-1 (ePSGL-1) primer (Xu et al., 2005) was used to amplify bovine cDNA synthesized from leukocyte total RNA. An ePSGL-1 primer sequence derived from the conserved homologous region between human and equine PSGL-1 (GI: 20987421 and GI: 34304193) was used for initial amplification of bPSGL-1. The total RNA was isolated by TRIZOL reagent (Invitrogen, Carlsbad, Calif.) following the manufacturer's instructions. Total RNA purity was determined spectrophometrically using the $A_{260}/A_{280}$ ratio and integrity was established with 2% agarose gel electrophoresis. The cDNA was synthesized with the Avian Myeloblastosis Virus (AMV) Reverse Transcriptase (Invitrogen) using both random hexamer and oligo dT primers. Upon generating a bPSGL-1 fragment, bovine gene-specific primers for the 3'- and 5'-rapid amplification of cDNA ends for (RACE) PCR were designed. A SMARTRace kit (Becton Dickinson, Palo Alto, Calif.) was used to amplify the rest of the open reading frame (ORF) and 3' and 5' untranslated regions (UTRs) of bPSGL-1 cDNA according to the manufacturer's instructions. All primers are listed in Table 1.

TABLE 1

Oligonucleotide Primer Sequences

| Primers | Sequences (5' to 3') | Location (bp) |
|---|---|---|
| Forward 1 | GTGAAGCAGTGCCTGCTGGCCA (SEQ. ID. NO: 7) | Equine 1027-1048 |
| Forward 2 | CTCTCCCGCAAGAACCACACAC ATACCCCGTG (SEQ. ID. NO: 8) | Equine 1111-1140 |
| Forward 3 | TGGTTTGCATCTCATCCCTGCTG (SEQ. ID. NO: 9) | Equine 1163-1185 |
| Forward 4 | CACCATGTTITCTGCAACTCCTG CTG (SEQ. ID. NO: 10) | Bovine 128-150 |
| Long | CTAATACGCATCACTATAGGGCA AGCAGTGGTATCAACGCAGAGT (SEQ. ID. NO: 11) | SMART Racer Kit |
| Short | CTAATACGACTCACTATAGGGCC GTAGCTGCGGGTTGGGTGGTCA (SEQ. ID. NO: 12) | SMART Racer Kit |
| Reverse 1 | AGGGAGGAAGCTGTGCAGGGTGA GGT (SEQ. ID. NO: 13) | Equine 1292-1314 |
| Reverse 2 | GAAAGGGAGGAAGCTGTGCAGGG TGA (SEQ. ID. NO: 14) | Bovine 1388-1413 |

The PCR products were run on agarose gel and the proper size bands were purified from the gel using the QIAEX II Gel Extraction Kit (Qiagen, Valencia, Calif.) and ligated into a pCR4-TOPO vector (Invitrogen, Carlsbad, Calif.). Positive clones were screened using PCR. Plasmids from the positive clones were sequenced with T7 or T3 promoter primers to characterize the full-length cDNA of bPSGL-1. All sequence reactions were performed in both directions. Nucleotide and amino acid identity and amino acid residue alignment were determined using the National Center for Biotechnology Information (NCBI) database.

The full-length cDNA sequence of bPSGL-1 (2108 bp) contains a 5' UTR (129 bp), a 3' UTR (695 bp), and a long ORF (1284 bp), encoding a predicted protein of 427 amino acids with a theoretical molecular weight of 45.3 kDa. The cDNA for bPSGL-1 suggests a protein of similar structure to the human and equine PSGL-1 protein: a hydrophobic $NH_2$-terminal signal peptide of 18 residues, mucin-like decameric repeats, a single unpaired extracellular cysteine occurring at position 335 in the extracellular domain, preceding the predicted single transmembrane-domain, a transmembrane segment of 23 residues and a cytoplasmic tail of 69 residues (SEQ. ID. NO: 1).

However, bPSGL-1 lacks a cleavage site for the paired basic amino acid-converting enzyme. As a result, there is likely no propeptide following the signal peptide and consequently the mature bPSG1-1 protein likely begins at residue 19. The homologies of the PSGL-1 amino acid sequences between equine (Xu et al., 2005), bovine, human (Sako et al., 1993) and mouse (Yang J. et al., 1996) are aligned and shown in FIG. 2.

There is approximately 52%, 49% and 40%, homology of bPSGL-1 to equine, human and mouse PSGL-1, respectively. Alignments of PSGL-1 between these different species indicated the sequences of signal peptide, transmembrane and cytoplasmic domains are much more highly conserved (72~77%, 86-95%, 65-72%, respectively), than the extracellular domain sequences (12~25%) in equine, human and bovine (FIG. 2). The extracellular domain of bPSGL-1 contains only 10-decameric repeats (residues 145-244) and two N-glycosylation sites located at positions 63 and 299 residues. This repeat region is also rich in serines, threonines, and prolines, characteristic of mucin-like domains with the consensus sequence A/L-T-E-A-L-S-T-E-P-X (SEQ. ID. NO: 15), where X can be either V, R, A, or K. It is obviously different in sequence from the human and equine PSGL-1 decameric repeats (see FIG. 1 and SEQ. ID. NO: 1). Furthermore, in the region of the N-terminus of bPSGL-1 (residues 19-55) corresponding to the P-selectin binding region of hPSGL-1, there are three tyrosines at residues 36, 49 and 51, which are located in an anionic consensus sequence that favors tyrosine sulfation.

According to the predictions of Bundgaard et al. (1997), a neutral or acidic charge of the residue in the amino terminal position (−1) of the tyrosine is critical for sulfation, whereas a basic residue will abolish it. The presence of the acidic residues $Asp^{48}$ and $Asp^{50}$ and the neutral residue $Leu^{35}$ at position −1 of $Tyr^{49}$, $Tyr^{51}$ and $Tyr^{36}$, respectively, in bPSGL-1 suggested that sulfation at either $Tyr^{49}$, $Tyr^{51}$ and/or $Tyr^{36}$ is likely.

Additionally, near the tyrosine sulfation sites, there are three threonine (Thr) residues $Thr^{25}$, $Thr^{28}$ and $Thr^{55}$, which could be O-glycosylated based on the prediction using NetOglyc network system (Hansen et al., 1998). $Thr^{25}$ and $Thr^{55}$ lie within eleven and six residues of $Tyr^{36}$ and $Tyr^{49}$, respectively, which are the same number of residues that separate $Tyr^{46}$ and $Tyr^{51}$ from $Thr^{57}$ in hPSGL-1 (FIG. 3). It is well known that both tyrosine sulfation and threonine O-glycosylation are required forhPSGL-1 binding to P-selectin. However, the specifics of tyrosine sulfation and threonine O-glycosylation for optimal binding of bPSGL-1 to P-selectin are unclear purely based on the original sequence analysis. Like murine PSGL-1 (mPSGL-1), it shares some degree of homology with hPSGL-1 in sequence, but Li et al. (1996) demonstrated that mPSGL-1 uses a different configuration of residues (Xia et al., 2003). Besides the important role of O-glycosylation in this P-selectin binding region, approximately 4.5% of the O-glycosylations in other regions of the extracellular domain of hPSGL-1 were reported to contribute to the interactions with P-selectin (Wilkins et al., 1996).

Thus, numerous Ser/Thr residues located in other regions of bPSGL-1 extracellular domain, indicating potential O-glycosylation, may also contribute to P-selectin binding by bPSGL-1. Additionally, O-glycosylation of hPSGL-1 represents one possible reason for the actual larger molecular weight (120 kDa) than its theoretical molecular weight of 42 kDa (ProtParam Software). bPSGL-1 is expected to actually be heavier than its theoretical molecular weight of 45.3 kDa.

In hPSGL-1, the epitope of PL1, a mAb to hPSGL-1, overlapped the P-selectin binding domain (Moore et al., 1995; Li et al., 1996). In the corresponding PL1 epitope region, bPSGL-1 shares 57% similarity to hPSGL-1, but little similarity (14.3%) was found with ePSGL-1 (FIG. 3). Based on this, flow cytometry was performed to test the cross-reactivity of PL1 with bovine and equine leukocytes, as previously reported (Xu et al., 2005). As mentioned above, after isolated bovine leukocytes were fixed with PFA (1% final concentration), they were stained with mouse $IgG_1$ anti-human CD162 (PL1) mAb (Beckman Coulter, Miami, Fla.) for 30 minutes on ice followed by a secondary phycoerythrin (PE)-conjugated rabbit anti-mouse IgG polyclonal Ab (Serotec, Raleigh, N.C.) for 30 minutes on ice. Control samples were stained with a PE-conjugated mouse $IgG_1$ mAb (Immunotech, Beckman Coulter Company, Paris, France) for 30 minutes on ice. All antibodies were diluted in PBS/BSA and contained either equine or newborn calf serum (5% final concentration). Fluorescence was measured on leukocyte populations, as confirmed by mouse IgG1 anti-bovine or anti-equine CD11a/18 plus PE-conjugated rabbit anti-mouse IgG polyclonal Ab staining, using a FACScan flow cytometer (Becton Dickinson, San Jose, Calif.) and analyzed using CellQuest (Becton Dickinson, San Jose, Calif.) software.

No cross-reactivity of PL1 was found with bovine (FIG. 4) or equine leukocytes (data not shown). This suggests a high species-specificity of this epitope region in Ab recognition, though they share some degree of homology in amino acid sequence. Moreover, because of the specific location of the PL1 epitope, which overlaps the putative P-selectin binding domain, a lack of cross-reactivity with PL1 in other species may also indicate the species-specificity of determining P-selectin binding. For example, although mPSGL-1 shares 50% homology with the PL1 epitope, it has been demonstrated that mPSGL-1 relies on a significantly different mechanism to regulate P-selectin binding (Xia et al., 2003).

In summary, bPSGL-1 is characterized as a protein containing an extracellular mucin-like domain, and transmembrane and cytoplasmic domains with homology to equine, human and mouse PSGL-1. However, the data suggests possible species-specific P-selectin binding. Further studies are required to clarify the detail of bPSGL-1 post-translational modification and the structures of oligosaccharides required for bPSGL-1 functionality. These studies should include glycosulfopeptides modeled after PSGL-1, where peptide sequence, sulfation and glycosylation can be changed precisely.

Experiment 2

Cloning Bovine PSGL-1 ORF

Total RNA from bovine monocytes will be activated for 24 hr with LPS (100 ng/ml) will be prepared with Trizol reagent (Sigma, St. Louis, Mo.). 1 μg total RNA will be reverse transcribed into cDNA using avian myeloblastic virus (AMV). The full-length of bovine PSGL-1 open reading frame (ORF) will be amplified by polymerase chain reaction (PCR) using primers for the known sequence of PSGL-1, as well as the unique restriction sites Xho I and BamH I on the 5' and 3' end respectively. The corresponding fragments will be purified by agarose electrophoresis and cloned into the TOPO vector (Invitrogen) to confirm the sequences. Thereafter, the fragment will be digested with Xho I and BamH I, and subcloned into pcDNA3.1-Myc-His expression vector (Life Technologies, Invitrogen).

Experiment 3

Transfecting and Expressing PSGL-1

CHOdhfr− cells expressing C2GnT, FucT-VII and C2GnT+FucT-VII will be maintained in Dulbecco's modified Eagle's medium (DMEM) containing 10% FBS, 1×HT (100 μM hypoxanthine, 16 μM thymidine), 1×NEAA (non-essential amino acids), 400 μg/ml G418, and 2 mM Gln at 37° C. in an atmosphere containing 5% $CO_2$. We will transfect the cells at 75-80% confluence with PSGL-1/Myc-His or series of bPSGL-1/Myc-His using GenePORTER 2 Transfection Reagent. Mock transfectants will receive pcDNA3.1-Myc-His without inserts. The cells will be split into selection medium (LS-DMEM, 10% FBS, 1×HT, 1 xNEAA, 600 μg/ml G418, 100 μg/ml hygromycin, 250 μg/ml Zeocin, and 2 mM Gln) 48 hr after transfection. Analysis of single colonies for expression of PSGL-1/Myc-His by flow cytometry will be performed to isolate stable clones. Human 562 kidney cells will be maintained in DMEM with 10% FBS and 2 mM Gln. Mock transfectants will receive pcDNA-V5-His without inserts. Two days after transfection, the cells will be transferred to selective medium. Colonies appear after about 2 weeks and will be screened by immunofluorescence microscopy for protein expression.

Experiment 4

Verifying PSGL-1 Expression

The PSGL-1 Expression can be verified using methods known to the art. However, in a preferred version, the PSGL-1 Expression is verified using one of the following techniques.

Polymerase Chain Reaction (PCR): To confirm successful transfection of PSGL-1-V5 gene in CHO cells, approximately 24 hr after transfection, the RNA of $1\times10^6$ cells will be isolated using the Trizol reagent (Sigma). One ug of RNA will be transcribed by 1st strand reverse transcriptase reaction using oligo $(dT)_{15}$ primer (Promega, Madison, Wis.) and SuperScript II reverse transcriptase (Gibco™, Invitrogen, Carlsbad, Calif.), following manufacturer's instructions. The cDNA of the transfected cells will be used as a template in subsequent PCR amplification for bovine PSGL-1. The PCR reaction will be carried out in a volume of 50 μl, containing 400 μM of each; nucleotides (dNTP) (Promega), 0.2 μmol of each primer in 1× Taq DNA polymerase buffer, and 2.5 U of recombinant Taq DNA polymerase (Gibco™, Invitrogen). The PCR products will be separated in 1% agarose gels containing 0.005% ethidium bromide (Sigma).

Intracellular staining: To confirm PSGL-1-V5 expression in CHO cells, CHO cells will be tested 24 hours after transfection by intracellular staining with an anti-v5 mAb (Invitrogen) and flow cytometric evaluation by FACScan (Becton Dickinson). A total of $1\times10^6$ transfected CHO cells will be washed with PBS and fixed in 2% formaldehyde at room temperature. After 20 min, the cells will be washed twice with PBS (100×g, 5 min) and subsequently stained with the myc-specific antibody diluted 1:50 in saponin-buffer (PBS, supplemented with 0.5% [w/v] bovine serum albumin (BSA), 0.5% [w/v] saponin (Sigma) and 0.02% [w/v] $NaN_3$ (Merck)) for 30 mM at room temperature. Then, the cells will be washed twice with saponin-buffer and stained with a PE-conjugated antimouse IgG1 (BD PharMingen, San Diego, Calif.) diluted 1:100 in saponin-buffer for 15 min at room temperature. Cells will be washed two more times and measured by FACScan. A similar strategy will be employed for detecting P-selectinN5-His expression on K562 cells with anti-V5 antibody.

Figure 5:
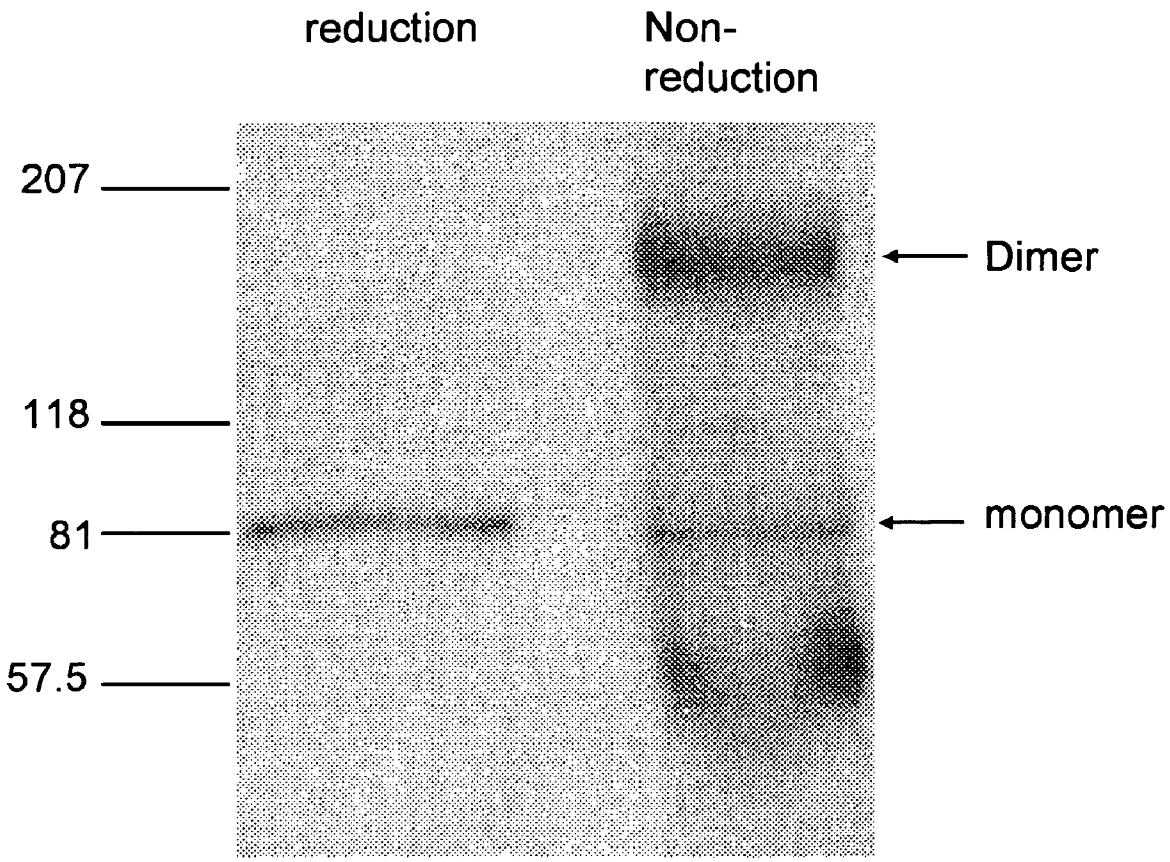
FIG. 5 illustrates immunoblots to detect the recombinant bPSGL-1 fusion protein.

SDS-PAGE and Western Blot: After 48-hrs transient transfection of CHO cells with pcDNA3.1-V5/His-TOPO expression vector containing bovine PSGL-1 ORF, the CHO cells were lysated (FIG. 5). Then, the samples were separated on 4-15% SDS gel (Bio-Rad) under reducing and non-reducing conditions, transferred to a PVDF-membrane, and detected with anti-V5 mAb (Invitrogen).

Specifically, to further confirm PSGL-1-V5 expression on the CHO cells surface, cells will be washed three times in HBSS, 0.1% $NaN_3$ and pelleted. Extracts will be prepared by resuspending the pellet in an equal volume of 2× solubilization buffer (40 mM MOPS, pH 7.5, 200 mM NaCl, 4 mM $CaCl_2$, 4 mM $MgCl_2$, 1% protein grade Triton X-100, 20 μg/ml leupeptin, 20 μg/ml aprotinin, 8 μg/ml pepstatin A, 10 mM benzamidine, 0.04% $NaN_3$). Phenylmethylsulfonyl fluoride will be added to the buffer to achieve a final concentration of 1 mM. The mixture will be incubated on ice for 45 min and then sonicated in an ice bath sonicator for 20 mM. A final sonication step will be done for 1-2 s using a Branson Sonifier/Cell Disruptor 185. The extracts will be spun at 16,000×g for 10 min, and the supernatant then transferred to a fresh tube. The protein concentration will be determined using a micro BCA assay (Bio-Rad). 250 μg of each cell extract will be boiled in sample buffer with or without 5% β-mercaptoethanol and loaded onto SDS-polyacrylamide gels. Electrophoresis will be carried out at 10 mA until samples reach the separating gel, at which time the current will be increased to 30 mA.

After SDS-PAGE, proteins will be transferred overnight at 20 volts to nitrocellulose membranes (0.2 μm) using the Bio-Rad minigel blotting apparatus. Membranes will be stained for 2 min with Ponceau S to determine the quality of the transfer, and the stacking gel interface will be marked. Blots will be destained in TBS (20 M Tris, NaCl, pH 7.5) and blocked with 5% non-fat dry milk in TTBS (TBS 0.05% Tween 20) for 1 h. Blots will be probed with anti-Myc in 0.5% non-fat dry milk/TTBS. The secondary antibody will be peroxidase-conjugated sheep anti-mouse IgG. Antibody incubations and washes will be performed according to ECL manufacturer's instructions. After addition of the ECL substrate, the blots will be exposed to Bio-Max MR film.

Experiment 5

Intracellular Staining/Flow Cytometric Analysis of Equine PSGL1-Ig Chimera

Figure 6C:
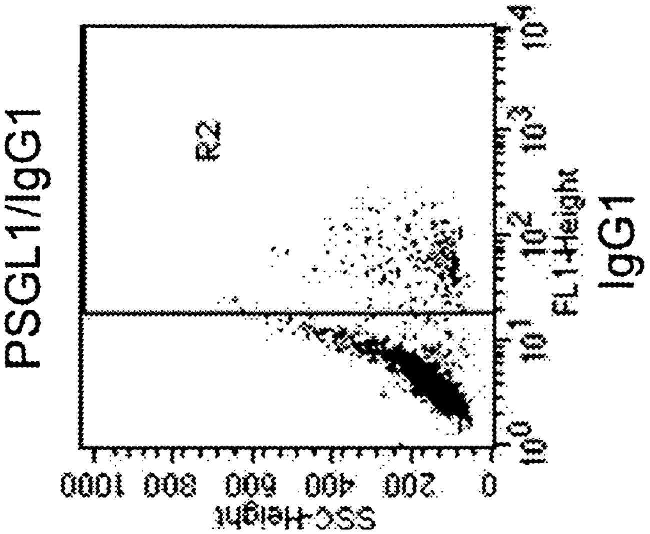
FIGS. 6A, 6B, and 6C illustrate intracellular staining and flow cytometric analysis of equine PSGL1-Ig chimera.
Figure 6B:
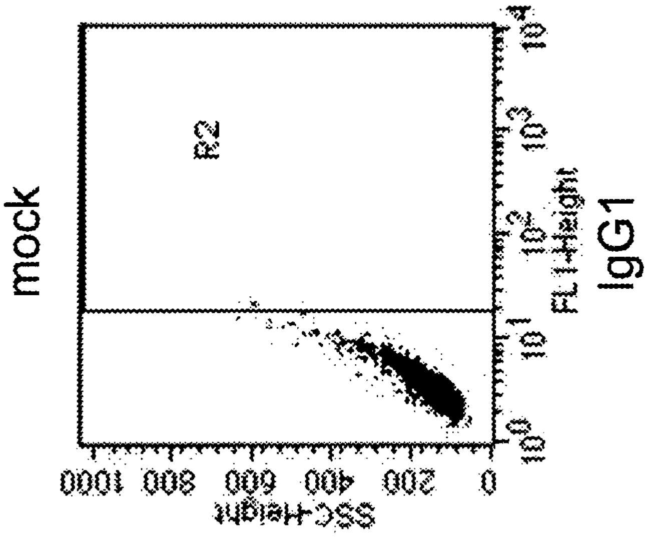
Figure 6A:
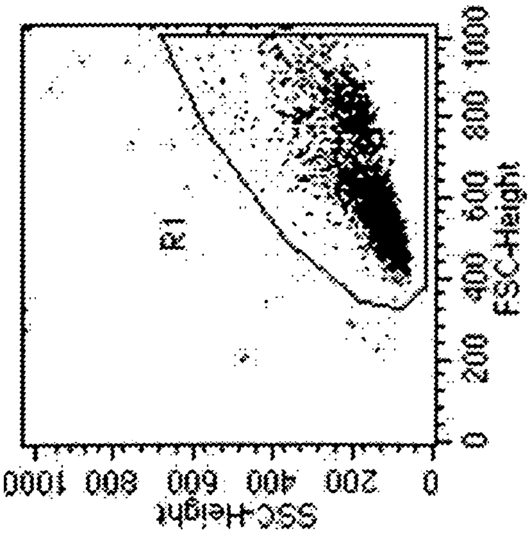

Referring now to FIGS. 6A, 6B, and 6C, intracellular staining and flow cytometric analysis of equine PSGL1-Ig chimera is shown. Here, CHO cells were transfected with a plasmid containing the extracellular domain of ePSGL-1 linked to equine heavy chain IgG1.

In FIG. 6A, CHO cells (R1) are gated based on typical forward and side scatter physical characteristics. In FIG. 6B (R2), gates are set to the negative control, meaning CHO cells transfected with pcDNAIGHG1 without insert. FIG. 6C shows CHO cells successfully transfected with ePSGL-1-IgG plasmid and expressed ePSGL-1-Ig protein, which binds to the CVS45 antibody, and subsequently recognized by Cy5 conjugated goat-anti mouse antibody.

Intracellular staining was performed in saponin buffer (PBS, supplements with 0.5% (w/v) BSA, 0.5% (w/v) saponin and 0.02% (w/v) $NaN_3$) using the monoclonal antibody CVS45 detecting bovie IgG1. The monoclonal CVS45 antibody was detected by Cy5 conjugated goat-anti mouse IgH (H+L) (Jackson ImmunoResearch Lab). Flow cytometry was performed using a FACS Calibur™ (Beckton Dickinson).

The goal is to define the binding domain of bovine PSGL-1 (bPSGL-1) and confirm that binding to bovine P-selectin results in signal transduction activation and inflammatory mediator biosynthesis in monocytes. If post-translational modifications of bPSGL-1 are responsible for high affinity binding to bovine P-selectin, the results of the cell binding assay will determine which CHO cell type will be used in subsequent experiments. To define the binding domain of bPSGL-1, we will express various deletion constructs of bPSGL-1 and evaluate relative binding to P-selectin (FIG. 7).

Experiment 6

Producing Bovine PSGL-1-Ig Chimeric Protein

Figure 7:
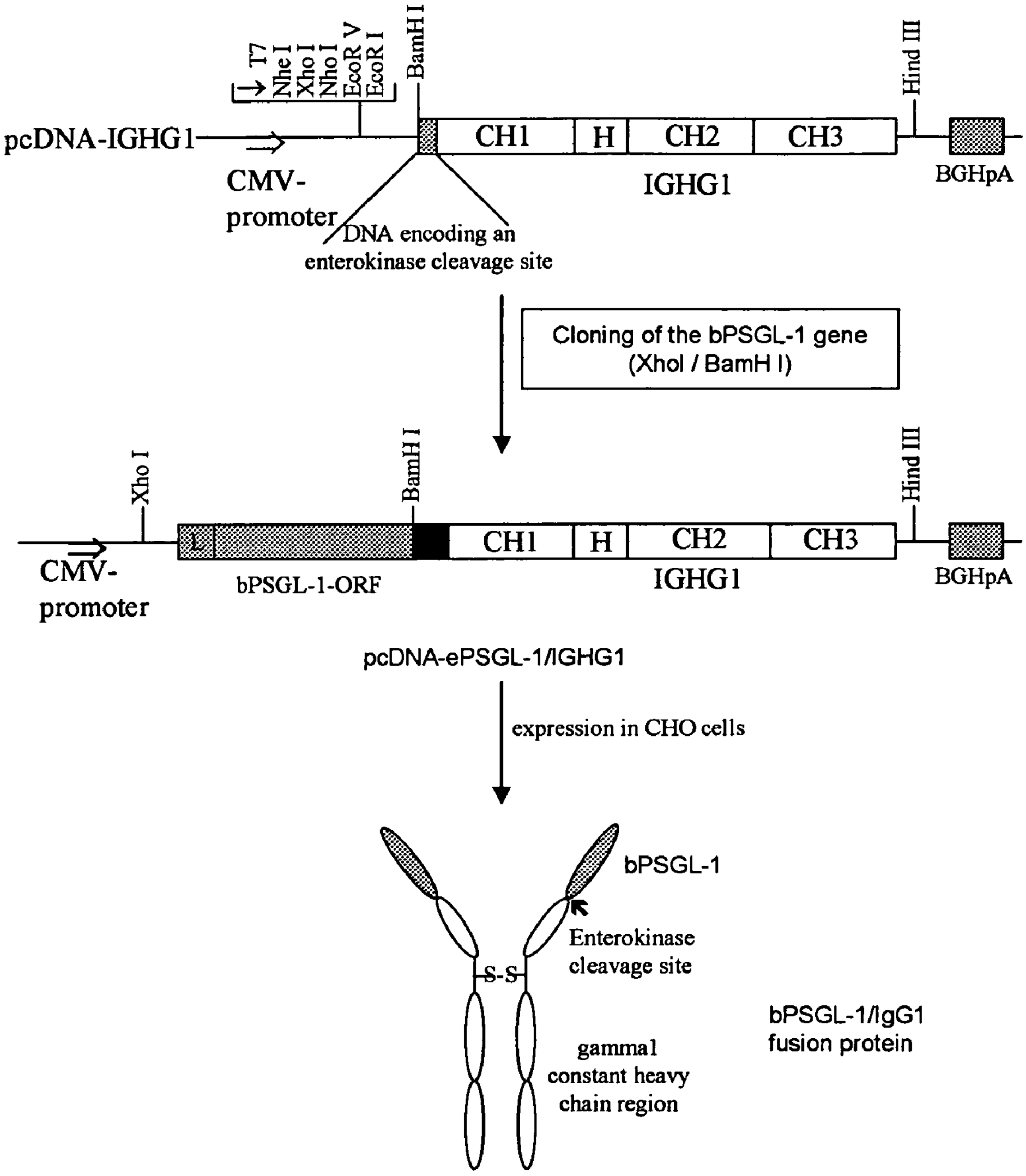
FIG. 7 is a schematic diagram depicting the cloning of bPSGL-1 into the expression vector.

Referring now to FIG. 7, the cloning site of the mammalian expression vector for equine IgG1 fusion proteins and a model of the recombinant fusion protein dimmer are shown. The expression vector (pcDNA-IGHG1) contains the equine IGHG1 gene including the coding sequence of the enterokinase cleavage site at the 5' end, and a multiple cloning site upstream of the BamHI site. XhoI restriction sites will be used together with BamHI for cloning of the bovine PSGL-1 gene. The examples discussed herein show the cloning of the bovine PSGL-1 gene into the expression vector. The pcDNA-bPSGL-1/IGHG1 construct encodes single chains, which form dimers resulting in the bPSGL-1/IgG1 fusion protein. BGHpA=bovine growth hormone polyadenylation signal; CH1, CH2, CH3=heavy chain constant gene exons; CMV=cytomegalovirus; H=hinge exon; IGHG1=immunoglobulin heavy chain constant gene encoding the IgG1 heavy chain constant region; L=leader sequence; T7=T7 primer site.

The bPSGL1-Ig fusion proteins will be expressed in CHO cells, and contain the bPSGL-1 signal peptide and binding domain, an enterokinase cleavage site (EKCS) linker and bovine $IgG_1$ heavy chain. The high producing clones will be selected, the expression identified, and the concentration tested by ELISA. The medium will be collected after 48 hr of additional culture and purify PSGL-1-Ig using ImmunoPure immobilized protein A (Pierce) according to the manufacturer's instructions.

Specifically, the bPSGL-1-IgG chimeric protein will be generated by the method comprising:

a) Inserting cDNA-encoding bPSGL-1-IgG extracellular domains into a pcDNA-IGHG1 expression vector containing an enterokinase digestion site $(Asp)_4$-Lys and the heavy chain of equine IgG1 (Wagner, B., et al, 2005);
b) Transiently transfecting the construct in K562 cells with GenePORTER 2 Transfection Reagent;
c) Collecting the supernatant and testing for fusion protein concentration by enzyme-linked immunosorbent assay (ELISA) using the CVS45 antibody;
d) Determining the amount of bPSGL-1-IgG secretion in the cell culture supernatant;
e) Purifying the secretion with a protein G affinity column; and
f) Collecting the recombinant bPSGL-1 by enterokinase digestion using Enterokinase Max™ (Invitrogen) following the manufacturer's instructions.

The CVS45 antibody of step (c) is specific for IgG1 (IgGa) and acts as a capture antibody. A secondary peroxidase conjugated goat anti-mouse IgG(H+L) antibody (Jackson ImmunoResearch Lab, West Grove, Pa.) acts as a detection antibody. Bovine IgG1, purified from bovine serum using a protein G affinity column, will be used to generate a standard curve.

Expected Results:

The RNA isolation, RT-PCR, plasmid cloning, sequencing, flow cytometry and Western Blotting techniques utilized herein are procedures with which we have extensive experience. Therefore, no impediments to constructing these aspects of the work are anticipated. To ensure successful use of the stable co-transfection and expression of bPSGL-1 in CHO cells, CHO cell lines permanently expressing C2GnT (core 2 β1-6-N-acetylglucosaminyltransferase) and FucTVII (α1-3 fucosyltransferase VII), which are required for bovine PSGL-1 functional expression in CHO cells, have been obtained. A way to determine the sequence of the PSGL-1 binding domain is to capture the native PSGL-1 binding domain by P-selectin affinity chromatography and directly analyzing the structure and predicting its sequence. This should allow the successful completion of the proposed experiments described in this section.

All the necessary reagents and CHO cell line for PSGL-1 co-transfection and expression have been obtained. The plasmid encoding the whole extracellular domain of bPSGL-1 in CHO cell has been successfully constructed and expressed. Its expression is being tracked by intracellular staining with flow cytometry.

It is understood that the invention is not confined to the particular construction and arrangement of parts herein illustrated and described, but embraces such modified forms thereof as come within the scope of the claims following the Bibliography. It is also understood that the terminology used herein is for the purpose of describing particular embodiments only, and is not intended to limit the scope of the present invention which will be limited only by the appended claims. It is further noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", "characterized by" and "having" can be used interchangeably.

BIBLIOGRAPHY

Bundgaard, J R, er al., 1997. New consensus features for tyrosine O-sulfation determined by mutational analysis. *J. Biol. Chem.* 272, 21700-21705.

Hansen, J E, et al., 1998. NetOglyc: prediction of mucin type O-glycosylation sites based on sequence context and surface accessibility. *Glycoconj.* 115, 115-130.

Hicks A E, et al., 2003. Recombinant P-selectin glycoprotein ligand-1 directly inhibits leukocyte rolling by all 3 selectins in vivo: complete inhibition of rolling is not required for anti-inflammatory effect. *Blood.,* 101:3249-56.

Jutila, M A, et al., 1994. Cell surface P- and E-selectin support shear-dependent rolling of bovine T cells. *J. Immunol.* 3917-3928.

Jutila, M A and Kurk, S., 1996. Analysis of bovine T cell interactions with E-, P-, and L-selectin: Characterization of lymphocyte on lymphocyte rolling and the effects of O-glycoprotease. *J. Immunol.* 289-296.

Li, F, et al., 1996. Visualization of P-selectin glycoprotein ligand-1 as a highly extended molecule and mapping of protein epitopes for monoclonal antibodies. *J. Biol. Chem.* 271, 6342-6348.

Middleton, J, et al., 2002. Leukocyte extravasation: chemokine transport and presentation by the endothelium. *Blood.* 100, 3853-3860.

Moore, K L, et al., 1995. P-selectin glycoprotein ligand-1 mediates rolling of human neutrophils on P-selectin. *J. Cell Biol.* 128, 661-671.

Morris D D, 1991. Endotoxemia in horses. *J Vet Intern Med* 5, 167-181.

Nguyen, M., et al., 1993. A role for sialyl Lewis-X/A glycoconjugates in capillary morphogenesis. *Nature.* 365, 267-269.

Olson, T S and Ley, K, 2002. Chemokines and chemokine receptors in leukocyte trafficking. *Am. J. Physiol. Regul. Integr. Comp. Physiol.* 283, R7-R28.

Paltrinieri, S, et al., 2004. Bovine Doppel (Dpl) and prion protein (PrP) expression on lymphoid tissue and circulating leukocytes. *J. Histochem. Cytochem.* 52, 1639-1645.

Roldan, V, et al., 2003. Soluble E-selectin in cardiovascular disease and its risk factors, A review of the literature. *Thromb. Haemost.* 90, 1007-1020.

Sako, D et al., 1993. Expression cloning of a functional glycoprotein ligand for P-selectin. *Cell.* 75, 1179-1186.

Smalley, D M and Ley, K, 2005. L-selectin: mechanisms and physiological significance of ectodomain cleavage. *J. Cell Mol. Med.* 9, 255-266.

Strubel, N A, et al., 1993. Isolation and characterization of a bovine cDNA encoding a functional homolog of human P-selectin. *Biochem. Biophys. Res. Commun.* 192, 338-344.

Tapper H, and Herwald H, 2000. Modulation of hemostatic mechanisms in bacterial infectious diseases. *Blood* 96:2329-2337.

Vandendries, E R, et al., 2004. Role of P-selectin and PSGL-1 in coagulation and thrombosis. *Thromb. Haemost.* 2004, 459-466

Walcheck, B, et al., 1992. Characterization of the bovine peripheral lymph node homing receptor: a lectin cell adhesion molecule (LECAM). *Eur. J. Immunol.* 22, 469-476.

Wagner, B, et al., 2005, Horse cytokine/IgG fusion proteins—mammalian expression of biologically active cytokines and a system to verify antibody specificity to equine cytokines. *Vet Immunology Immunopathology,* 105(1-2):1-14

Weiss D J and Rashid J, 1998. The sepsis-coagulant axis: A review. *J Vet Intern Med* 12, 317-324.

Welch R D, et al., 1992. Disseminated intravascular coagulation associated with colic in 23 horses (1984-1989). *J Vet Inetrn Med* 6, 29-35.

Wilkins, P P, et al., 1996. Structures of the O-glycans on P-selectin glycoprotein ligand-1 from HL-60 cells. *J. Biol. Chem.* 271, 8732-8742.

Xia, L, et al., 2003. N-terminal residues in murine P-selectin glycoprotein ligand-1 required for binding to murine P-selectin. *Blood.* 101, 552-559.

Xu, J, et al., 2005. Identification of equine P-selectin glycoprotein ligand-1 (CD162). *Mamm. Genome.* 16, 66-71.

Yang, J, et al., 1996. Mouse P-selectin glycoprotein ligand-1: molecular cloning, chromosomal localization, and expression of a functional P-selectin receptor. *Blood.* 87, 4176-4186.

What is claimed is:

1. An isolated polypeptide comprising:

(a) an amino acid sequence comprising residues 1 to 317 of SEQ. ID. NO: 2 encoding a protein capable of binding bovine P-selectin; or (b) a polypeptide fragment comprising at least 10 contiguous amino acid residues of residues 1 to 317 of SEQ. ID. NO: 2.

2. The isolated polypeptide of claim 1, which is modified by sulfation, glycosylation, or both.

3. The isolated polypeptide of claim 1 further comprising a heterologous sequence derived from an immunoglobulin.

4. The isolated polypeptide of claim 3, which is modified by sulfation, glycosylation, or both.

5. A composition comprising, in combination, a polypeptide including a bovine P-selectin glycoprotein ligand-1 (bPSGL-1) and a pharmaceutically-acceptable carrier, wherein the polypeptide comprises:

(a) an amino acid sequence comprising residues 1 to 317 of SEQ. ID. NO: 2 encoding a protein capable of binding bovine P-selectin; or (b) a polypeptide fragment comprising at least 10 contiguous amino acid residues of residues 1 to 317 of SEQ. ID. NO: 2.

6. The composition of claim 5 wherein the polypeptide further includes a heterologous amino acid sequence derived from an immunoglobulin.

7. The composition of claim 5, wherein the polypeptide is modified by sulfation, glycosylation, or both.

8. The composition of claim 6, wherein the polypeptide is modified by sulfation, glycosylation, or both.

9. An isolated polypeptide comprising an amino acid sequence including residues 1 to 409 of SEQ. ID. NO: 2.

10. The isolated polypeptide of claim 9, which is modified by sulfation, glycosylation, or both.

11. The isolated polypeptide of claim 9 further comprising a heterologous sequence derived from an immunoglobulin.

12. The isolated polypeptide of claim 11, which is modified by sulfation, glycosylation, or both.

13. A method of producing bovine P-selectin glycoprotein ligand-1 (bPSGL-1)-IgG chimeric protein, the method comprising:

a) inserting cDNA encoding a bPSGL-1 extracellular domain into an expression vector containing an enterokinase digestion site to define an expression construct, the extracellular domain including an amino acid sequence comprising residues 1 to 317 of SEQ. ID. NO: 2;

b) transfecting the expression construct into a host cell;

c) determining presence of bPSGL-1-IgG secretion;

d) purifying secreted bPSGL-1-IgG with an affinity column; and e) collecting purified bPSGL-1-IgG by enterokinase digestion.

* * * * *

SEQUENCE LISTING

<160> NUMBER OF SEQ ID NOS: 19

<210> SEQ ID NO 1
<211> LENGTH: 2108
<212> TYPE: DNA
<213> ORGANISM: Bovine P-selectin glycoprotein ligand-1
<220> FEATURE:
<221> NAME/KEY: CDS
<222> LOCATION: (130)..(1410)
<220> FEATURE:
<221> NAME/KEY: sig_peptide
<222> LOCATION: (130)..(183)
<220> FEATURE:
<221> NAME/KEY: mat_peptide
<222> LOCATION: (184)..(1410)
<220> FEATURE:
<221> NAME/KEY: PSGL-1/P-selectin-interaction-region
<222> LOCATION: (184)..(294)
<220> FEATURE:
<221> NAME/KEY: potential_N-linked_glycosylation_site
<222> LOCATION: (316)..(324)
<220> FEATURE:
<221> NAME/KEY: mucin-like_domain
<222> LOCATION: (562)..(861)
<220> FEATURE:
<221> NAME/KEY: potential_N-linked_glycosylation_site
<222> LOCATION: (1024)..(1032)
<220> FEATURE:
<221> NAME/KEY: trans-membrane_domain
<222> LOCATION: (1135)..(1203)
<220> FEATURE:
<221> NAME/KEY: polyA_site
<222> LOCATION: (2079)..(2083)

<400> SEQUENCE: 1

```
acgcgggaag cagtggtatc aacgcagagt acgcggggag cacaggctga gtccttgtcg      60

ctaaagcaga ggaaccactt ctcctgggcc cacgaggtgg ctgtcccatg gtctgctgag     120

cacggtgcc atg ttt ctg caa ctc ctg ctg ctt ctg gcc ctg ctg ggc cct     171
          Met Phe Leu Gln Leu Leu Leu Leu Leu Ala Leu Leu Gly Pro
                      -15                 -10                 -5

ggc agc agc cac cag ctg ggg gag acc agc acg aat gaa act gtg aag       219
Gly Ser Ser His Gln Leu Gly Glu Thr Ser Thr Asn Glu Thr Val Lys
            -1  1               5                   10

gcc cca ggc ccc cta tac cca ggt gag gag aga gac cca gaa gac gat       267
Ala Pro Gly Pro Leu Tyr Pro Gly Glu Glu Arg Asp Pro Glu Asp Asp
        15                  20                  25

gaa gac tat gac tat ata gga caa acg gac cct cca gag atg ctt gac       315
Glu Asp Tyr Asp Tyr Ile Gly Gln Thr Asp Pro Pro Glu Met Leu Asp
    30                  35                  40

aat atc act gag gtc ccc aag ttt ctg cct atg gtg aca acg ctg ggg       363
Asn Ile Thr Glu Val Pro Lys Phe Leu Pro Met Val Thr Thr Leu Gly
45                  50                  55                  60

cag aga gag tct gca ggg cct atg att cct gag tca ttc att ctg gag       411
Gln Arg Glu Ser Ala Gly Pro Met Ile Pro Glu Ser Phe Ile Leu Glu
                65                  70                  75

gtg tcc aca agg gac tct gct gtc ctg agt gcc aca ggg gca acc acc       459
Val Ser Thr Arg Asp Ser Ala Val Leu Ser Ala Thr Gly Ala Thr Thr
            80                  85                  90

aaa aaa ctg agt cca aaa ctg gtc aca ccg gtc ccg ctg acc aaa gaa       507
Lys Lys Leu Ser Pro Lys Leu Val Thr Pro Val Pro Leu Thr Lys Glu
        95                  100                 105

ctg gtt act gaa atc cct ccc aaa gtg aag gat cca tcc aca gag ctg       555
Leu Val Thr Glu Ile Pro Pro Lys Val Lys Asp Pro Ser Thr Glu Leu
    110                 115                 120
```

-continued

```
gct gcg gcc aca gag gcc ctg tcc aca gac ccc gtg acc aca gag gcc      603
Ala Ala Ala Thr Glu Ala Leu Ser Thr Asp Pro Val Thr Thr Glu Ala
125                 130                 135                 140

ctg tcc acg gaa ccc agg ctt aca gaa gcc ctg tcc aca gaa ccc gtg      651
Leu Ser Thr Glu Pro Arg Leu Thr Glu Ala Leu Ser Thr Glu Pro Val
                145                 150                 155

gcc aca gag gtc ctg tcc acg gaa ccc agg ctt aca gaa gcc ctg tcc      699
Ala Thr Glu Val Leu Ser Thr Glu Pro Arg Leu Thr Glu Ala Leu Ser
            160                 165                 170

aca gaa cct gca gcc aca gag gcc ctg tcc acg gaa ccc agg ctt aca      747
Thr Glu Pro Ala Ala Thr Glu Ala Leu Ser Thr Glu Pro Arg Leu Thr
        175                 180                 185

gag gcc ctg tcc aca gaa ccc agg ctt aca gaa gcc ctg tcc acg gaa      795
Glu Ala Leu Ser Thr Glu Pro Arg Leu Thr Glu Ala Leu Ser Thr Glu
    190                 195                 200

ccc gca gcc aca gag tcc ctg tcc aca gaa ccc aaa atc aca gag act      843
Pro Ala Ala Thr Glu Ser Leu Ser Thr Glu Pro Lys Ile Thr Glu Thr
205                 210                 215                 220

ctg ccc acg gaa ccg gcc acc aca gaa gcc cct ttc agg gag ccc act      891
Leu Pro Thr Glu Pro Ala Thr Thr Glu Ala Pro Phe Arg Glu Pro Thr
                225                 230                 235

acc ata cca gcc ctg ccc aca gat cca acc act gtg gag gcc ctg ccc      939
Thr Ile Pro Ala Leu Pro Thr Asp Pro Thr Thr Val Glu Ala Leu Pro
            240                 245                 250

acg aga act gct acc aca agg ggc cta acc aca gcc ctt cct gtg gcc      987
Thr Arg Thr Ala Thr Thr Arg Gly Leu Thr Thr Ala Leu Pro Val Ala
        255                 260                 265

tct gat act ccc aag ggc acc act gtg gca gct ggc aac ttg tct gat     1035
Ser Asp Thr Pro Lys Gly Thr Thr Val Ala Ala Gly Asn Leu Ser Asp
    270                 275                 280

gac ttc act ggg aac aaa gat cat agc ctt ttt ccc tgg agc tct gtg     1083
Asp Phe Thr Gly Asn Lys Asp His Ser Leu Phe Pro Trp Ser Ser Val
285                 290                 295                 300

gcc cca ctc ccc gca gac ggc ctg cca gac ccg ggc ccc gtg aag cag     1131
Ala Pro Leu Pro Ala Asp Gly Leu Pro Asp Pro Gly Pro Val Lys Gln
                305                 310                 315

tgt ttg ctg gcc atc ctc atc ctg gcc ctg ctg gcc acc atc ttc ctc     1179
Cys Leu Leu Ala Ile Leu Ile Leu Ala Leu Leu Ala Thr Ile Phe Leu
            320                 325                 330

gtg tgc act gtg gtg ctg gcc atc cgc ctc tcc cgc aag gac cac ctg     1227
Val Cys Thr Val Val Leu Ala Ile Arg Leu Ser Arg Lys Asp His Leu
        335                 340                 345

tac ccc gtg cgc gat tac tcc ccc agc gag atg gtc tgc atc tca tct     1275
Tyr Pro Val Arg Asp Tyr Ser Pro Ser Glu Met Val Cys Ile Ser Ser
    350                 355                 360

ctg ctg ccc gag cgg ggc gag ggg cct gcg ccc gtg ccc aac ggg gac     1323
Leu Leu Pro Glu Arg Gly Glu Gly Pro Ala Pro Val Pro Asn Gly Asp
365                 370                 375                 380

ctg ccc aag gcc agg gaa cag ggc cgg aag gcg ggg ccg agg gag ggc     1371
Leu Pro Lys Ala Arg Glu Gln Gly Arg Lys Ala Gly Pro Arg Glu Gly
                385                 390                 395

cgt gaa ggg gat gac ctc acc ctg cac agc ttc ctc cct tagctcccga      1420
Arg Glu Gly Asp Asp Leu Thr Leu His Ser Phe Leu Pro
            400                 405

gctgctgagc caaggcccat gccgaggctc taagccctgg gtcaggctgc cttggatccc   1480

cctggagacg ggaatcttca gggcggggac ccgggctgcc acacacaaga ctgagagcag   1540

ccaggctcca ggcactgaag caggcctggc aaacagaacc tccggtagag gctgcagacg   1600

accccccagc tccctgccca gcccccgtgt gtcctgggct ccctctaatg cctccgttcc   1660
```

-continued

```
ctggccactg gagtctcatc ctcacgcacc caggaggact cagagttcgt ccctgctgcc   1720

atgcccgcta ccgtttcctt ctacggtcac tgcacaggga gggggcactc tgaactgcat   1780

tccttagttc actttctatc accccccgct cctcatttgg gctatctctc agggaaccca   1840

cggtgagttg tgggggctga gtaggttcct taggggactc tgtggaccta caagctattg   1900

tctagtgcca gcctaatccc atcctgccct ccctcgcctc cccccccggg gccttgattg   1960

aggtgctcgc agaggtctcc cgccacccag ctcagggccc aggacgacac acacacacac   2020

acacacacac acacacgtcg ctcagtcatg tccgactctc tgcgacccca tgacggtcag   2080

taaatgtttt ggtggtgatc aaaaaaaa                                      2108
```

<210> SEQ ID NO 2
<211> LENGTH: 427
<212> TYPE: PRT
<213> ORGANISM: Bovine P-selectin glycoprotein ligand-1

<400> SEQUENCE: 2

```
Met Phe Leu Gln Leu Leu Leu Leu Leu Ala Leu Leu Gly Pro Gly Ser
            -15                 -10                 -5

Ser His Gln Leu Gly Glu Thr Ser Thr Asn Glu Thr Val Lys Ala Pro
    -1  1               5                   10

Gly Pro Leu Tyr Pro Gly Glu Glu Arg Asp Pro Glu Asp Asp Glu Asp
15                  20                  25                  30

Tyr Asp Tyr Ile Gly Gln Thr Asp Pro Pro Glu Met Leu Asp Asn Ile
                35                  40                  45

Thr Glu Val Pro Lys Phe Leu Pro Met Val Thr Thr Leu Gly Gln Arg
            50                  55                  60

Glu Ser Ala Gly Pro Met Ile Pro Glu Ser Phe Ile Leu Glu Val Ser
        65                  70                  75

Thr Arg Asp Ser Ala Val Leu Ser Ala Thr Gly Ala Thr Thr Lys Lys
    80                  85                  90

Leu Ser Pro Lys Leu Val Thr Pro Val Pro Leu Thr Lys Glu Leu Val
95                  100                 105                 110

Thr Glu Ile Pro Pro Lys Val Lys Asp Pro Ser Thr Glu Leu Ala Ala
                115                 120                 125

Ala Thr Glu Ala Leu Ser Thr Asp Pro Val Thr Thr Glu Ala Leu Ser
            130                 135                 140

Thr Glu Pro Arg Leu Thr Glu Ala Leu Ser Thr Glu Pro Val Ala Thr
        145                 150                 155

Glu Val Leu Ser Thr Glu Pro Arg Leu Thr Glu Ala Leu Ser Thr Glu
    160                 165                 170

Pro Ala Ala Thr Glu Ala Leu Ser Thr Glu Pro Arg Leu Thr Glu Ala
175                 180                 185                 190

Leu Ser Thr Glu Pro Arg Leu Thr Glu Ala Leu Ser Thr Glu Pro Ala
                195                 200                 205

Ala Thr Glu Ser Leu Ser Thr Glu Pro Lys Ile Thr Glu Thr Leu Pro
            210                 215                 220

Thr Glu Pro Ala Thr Thr Glu Ala Pro Phe Arg Glu Pro Thr Thr Ile
        225                 230                 235

Pro Ala Leu Pro Thr Asp Pro Thr Thr Val Glu Ala Leu Pro Thr Arg
    240                 245                 250

Thr Ala Thr Thr Arg Gly Leu Thr Thr Ala Leu Pro Val Ala Ser Asp
255                 260                 265                 270
```

-continued

Thr Pro Lys Gly Thr Thr Val Ala Ala Gly Asn Leu Ser Asp Asp Phe
275 280 285

Thr Gly Asn Lys Asp His Ser Leu Phe Pro Trp Ser Ser Val Ala Pro
290 295 300

Leu Pro Ala Asp Gly Leu Pro Asp Pro Gly Pro Val Lys Gln Cys Leu
305 310 315

Leu Ala Ile Leu Ile Leu Ala Leu Leu Ala Thr Ile Phe Leu Val Cys
320 325 330

Thr Val Val Leu Ala Ile Arg Leu Ser Arg Lys Asp His Leu Tyr Pro
335 340 345 350

Val Arg Asp Tyr Ser Pro Ser Glu Met Val Cys Ile Ser Ser Leu Leu
355 360 365

Pro Glu Arg Gly Glu Gly Pro Ala Pro Val Pro Asn Gly Asp Leu Pro
370 375 380

Lys Ala Arg Glu Gln Gly Arg Lys Ala Gly Pro Arg Glu Gly Arg Glu
385 390 395

Gly Asp Asp Leu Thr Leu His Ser Phe Leu Pro
400 405

<210> SEQ ID NO 3
<211> LENGTH: 420
<212> TYPE: PRT
<213> ORGANISM: Equine PGSL-1

<400> SEQUENCE: 3

Met Pro Leu Pro Leu Leu Leu Leu Leu Ser Leu Leu Gly Pro Gly Ser
1 5 10 15

Arg Leu Gln Leu Val Arg Gly Gln Thr Gly Val Ser Lys Tyr Leu His
20 25 30

Arg Asp Asp Val Asn Arg Glu Gly Thr Asp Leu Leu Lys Thr Pro Glu
35 40 45

Ser Ser Thr Lys Thr Phe Ser Leu Ser Pro Arg Leu Leu Asp Val Met
50 55 60

Gly Thr Pro Glu Gln Arg Asp Ser Thr Gly Pro Gly Thr Pro Glu Pro
65 70 75 80

Ala Thr Leu Glu Val Ala Met Glu Asp Ser Ala Gly Leu Gly Ala Gly
85 90 95

Gly Thr Ala Val Gly Asn Leu Thr Thr Glu Leu Ala Thr Gln Gly Ile
100 105 110

Ser Val Thr Met Gly Pro Leu Thr Glu Gly Leu Val Thr Thr Asn Pro
115 120 125

Pro Phe Leu Glu Ala Leu Ser Thr Asp Gly Ala Gln Ser Thr Glu Leu
130 135 140

Asp Thr Leu Glu Ala Leu Ser Thr Gly Pro Ala Ala Thr Glu Ala Leu
145 150 155 160

Thr Thr Gln Pro Ala Ala Thr Glu Val Leu Ser Thr Glu Pro Ala Ala
165 170 175

Thr Glu Ala Leu Thr Thr Gln Pro Ala Ala Thr Glu Val Leu Ser Thr
180 185 190

Glu Pro Ala Ala Thr Glu Ala Leu Thr Thr Gln Pro Ala Ala Thr Glu
195 200 205

Val Leu Ser Thr Glu Pro Ala Ala Thr Glu Ala Leu Thr Ser Gln Pro
210 215 220

Ala Ala Thr Glu Val Leu Ser Lys Gly Pro Ala Ala Thr Glu Ala Leu
225 230 235 240

-continued

Thr Thr Gln Pro Ala Ala Thr Glu Val Leu Ser Thr Glu Pro Ala Ala
245 250 255

Thr Glu Ala Leu Thr Ser Gln Pro Ala Ala Thr Glu Val Leu Ser Lys
260 265 270

Gly Pro Ala Ala Thr Glu Ala Leu Thr Thr Gln Pro Ala Val Thr Glu
275 280 285

Ala Gln Ser Thr Val Leu Ala Thr Thr Ser Phe Arg Gly Lys Ser Gln
290 295 300

Thr Val Ser Leu Leu Ser Ser Thr Val Pro Asn Pro Thr Val Ala Trp
305 310 315 320

Asp His Ile Pro Val Lys Gln Cys Leu Leu Ala Ile Leu Ile Leu Ala
325 330 335

Leu Leu Ala Thr Ile Phe Leu Val Cys Thr Val Val Leu Ala Val Arg
340 345 350

Leu Ser Arg Lys Asn His Thr Tyr Pro Val Arg Ser Tyr Ser Pro Thr
355 360 365

Glu Met Val Cys Ile Ser Ser Leu Leu Pro Glu Gly Gly Glu Gly Pro
370 375 380

Thr Thr Thr Ala Asn Gly Gly Leu Pro Thr Pro Lys Gly Arg Gly Arg
385 390 395 400

Lys Ala Gly Pro Gly Glu Asp His Asp Gly Asp Asp Leu Thr Leu His
405 410 415

Ser Phe Leu Pro
420

<210> SEQ ID NO 4
<211> LENGTH: 427
<212> TYPE: PRT
<213> ORGANISM: Bovine PGSL-1

<400> SEQUENCE: 4

Met Phe Leu Gln Leu Leu Leu Leu Leu Ala Leu Leu Gly Pro Gly Ser
1 5 10 15

Ser His Gln Leu Gly Glu Thr Ser Thr Asn Glu Thr Val Lys Ala Pro
20 25 30

Gly Pro Leu Tyr Pro Gly Glu Glu Arg Asp Pro Glu Asp Asp Glu Asp
35 40 45

Tyr Asp Tyr Ile Gly Gln Thr Asp Pro Pro Glu Met Leu Asp Asn Ile
50 55 60

Thr Glu Val Pro Lys Phe Leu Pro Met Val Thr Thr Leu Gly Gln Arg
65 70 75 80

Glu Ser Ala Gly Pro Met Ile Pro Glu Ser Phe Ile Leu Glu Val Ser
85 90 95

Ser Thr Arg Asp Ser Ala Val Leu Ser Ala Thr Gly Ala Thr Thr Lys
100 105 110

Lys Leu Ser Pro Lys Leu Val Thr Pro Val Pro Leu Ile Lys Glu Leu
115 120 125

Val Thr Glu Ile Pro Pro Lys Val Lys Asp Pro Ser Thr Glu Leu Ala
130 135 140

Ala Ala Thr Glu Ala Leu Ser Thr Asp Pro Val Thr Thr Glu Ala Leu
145 150 155 160

Ser Thr Glu Pro Arg Leu Thr Glu Ala Leu Ser Thr Glu Pro Val Ala
165 170 175

Thr Glu Val Leu Ser Thr Glu Pro Arg Leu Thr Glu Ala Leu Ser Thr

-continued

```
            180                 185                 190

Glu Pro Ala Ala Thr Glu Ala Leu Ser Thr Glu Pro Arg Leu Thr Glu
        195                 200                 205

Ala Leu Ser Thr Glu Pro Arg Leu Thr Glu Ala Leu Ser Thr Glu Pro
    210                 215                 220

Ala Ala Thr Glu Ser Leu Ser Thr Glu Pro Lys Ile Thr Glu Thr Leu
225                 230                 235                 240

Pro Thr Glu Pro Ala Thr Thr Glu Ala Pro Phe Arg Glu Pro Thr Thr
                245                 250                 255

Ile Pro Ala Leu Pro Thr Asp Pro Thr Thr Val Glu Ala Leu Pro Thr
            260                 265                 270

Arg Thr Ala Thr Thr Arg Gly Leu Thr Thr Ala Leu Pro Val Ala Ser
        275                 280                 285

Asp Thr Pro Lys Gly Thr Thr Val Ala Ala Gly Asn Leu Ser Asp Asp
    290                 295                 300

Phe Thr Gly Asn Lys Asp His Ser Leu Phe Pro Trp Ser Ser Val Ala
305                 310                 315                 320

Pro Leu Pro Ala Asp Gly Leu Pro Asp Pro Gly Pro Val Lys Gln Cys
                325                 330                 335

Leu Leu Ala Ile Leu Ile Leu Ala Leu Leu Ala Thr Ile Phe Leu Val
            340                 345                 350

Cys Thr Val Val Leu Ala Ile Arg Leu Ser Arg Lys Asp His Leu Tyr
        355                 360                 365

Pro Val Arg Asp Ser Pro Ser Glu Met Val Cys Ile Ser Ser Leu Leu
    370                 375                 380

Pro Glu Arg Gly Glu Gly Pro Ala Pro Val Pro Asn Gly Asp Leu Pro
385                 390                 395                 400

Lys Ala Arg Glu Gln Gly Arg Lys Ala Gly Pro Arg Glu Gly Arg Glu
                405                 410                 415

Gly Asp Asp Leu Thr Leu His Ser Phe Leu Pro
            420                 425


<210> SEQ ID NO 5
<211> LENGTH: 402
<212> TYPE: PRT
<213> ORGANISM: Human PGSL-1

<400> SEQUENCE: 5

Met Pro Leu Gln Leu Leu Leu Leu Leu Ile Leu Leu Gly Pro Gly Asn
1               5                   10                  15

Ser Leu Gln Leu Trp Asp Thr Trp Ala Asp Glu Ala Glu Lys Ala Leu
            20                  25                  30

Gly Pro Leu Leu Ala Arg Asp Arg Arg Gln Ala Thr Glu Tyr Glu Tyr
        35                  40                  45

Leu Asp Tyr Asp Phe Leu Pro Glu Thr Glu Pro Pro Glu Met Asn Arg
    50                  55                  60

Leu Ser Thr Asp Thr Thr Pro Leu Thr Gly Pro Gly Thr Pro Glu Ser
65                  70                  75                  80

Thr Thr Val Glu Pro Ala Ala Arg Arg Ser Thr Gly Leu Asp Ala Gly
                85                  90                  95

Gly Ala Val Thr Glu Leu Thr Thr Glu Leu Ala Asn Met Gly Asn Leu
            100                 105                 110

Ser Thr Asp Ser Ala Ala Met Glu Ile Gln Thr Thr Gln Pro Ala Ala
        115                 120                 125
```

-continued

```
Thr Glu Ala Gln Thr Thr Pro Leu Ala Ala Thr Glu Ala Gln Thr Thr
    130                 135                 140

Arg Leu Thr Ala Thr Glu Ala Gln Thr Thr Pro Leu Ala Ala Thr Glu
145                 150                 155                 160

Ala Gln Thr Thr Pro Pro Ala Ala Thr Glu Ala Gln Thr Thr Gln Pro
                165                 170                 175

Thr Gly Leu Glu Ala Gln Thr Thr Ala Pro Ala Ala Met Glu Ala Gln
            180                 185                 190

Thr Thr Ala Pro Ala Ala Met Glu Ala Gln Thr Thr Pro Pro Ala Ala
        195                 200                 205

Met Glu Ala Gln Thr Thr Gln Thr Thr Ala Met Glu Ala Gln Thr Thr
    210                 215                 220

Ala Pro Glu Ala Thr Glu Ala Gln Thr Thr Gln Pro Thr Ala Thr Glu
225                 230                 235                 240

Ala Gln Thr Ile Pro Leu Ala Ala Met Glu Ala Leu Ser Thr Glu Pro
                245                 250                 255

Ser Ala Thr Glu Ala Leu Ser Met Glu Pro Thr Thr Lys Arg Gly Leu
            260                 265                 270

Phe Ile Pro Phe Ser Val Ser Ser Val Thr His Lys Gly Ile Pro Met
        275                 280                 285

Ala Ala Ser Asn Leu Ser Val Asn Tyr Pro Val Gly Ala Pro Asp His
    290                 295                 300

Ile Ser Val Lys Gln Cys Leu Leu Ala Ile Leu Ile Leu Ala Leu Val
305                 310                 315                 320

Ala Thr Ile Phe Phe Val Cys Thr Val Val Leu Ala Val Arg Leu Ser
                325                 330                 335

Arg Lys Gly His Met Tyr Pro Val Arg Asn Tyr Ser Pro Thr Glu Met
            340                 345                 350

Val Cys Ile Ser Ser Leu Leu Pro Asp Gly Gly Glu Gly Pro Ser Ala
        355                 360                 365

Thr Ala Asn Gly Gly Leu Ser Lys Ala Lys Ser Pro Gly Leu Thr Pro
    370                 375                 380

Glu Pro Arg Glu Asp Arg Glu Gly Asp Asp Leu Thr Leu His Ser Phe
385                 390                 395                 400

Leu Pro


<210> SEQ ID NO 6
<211> LENGTH: 397
<212> TYPE: PRT
<213> ORGANISM: Murine PGSL-1

<400> SEQUENCE: 6

Met Ser Pro Ser Phe Leu Val Leu Leu Thr Ile Leu Gly Pro Gly Asn
1               5                   10                  15

Ser Leu Gln Leu Gln Asp Pro Trp Gly His Glu Thr Lys Glu Ala Pro
            20                  25                  30

Gly Pro Val His Leu Arg Glu Arg Arg Gln Val Val Gly Asp Asp Asp
        35                  40                  45

Phe Glu Asp Pro Asp Tyr Thr Tyr Asn Thr Asp Pro Pro Glu Leu Leu
    50                  55                  60

Lys Asn Val Thr Asn Thr Val Ala Ala His Pro Glu Leu Pro Thr Thr
65                  70                  75                  80

Val Val Met Leu Glu Arg Asp Ser Thr Ser Ala Gly Thr Ser Glu Arg
                85                  90                  95
```

-continued

```
Ala Thr Glu Lys Ile Ala Thr Thr Asp Pro Thr Ala Pro Gly Thr Gly
            100                 105                 110

Gly Thr Ala Val Gly Met Leu Ser Thr Asp Ser Ala Thr Gln Trp Ser
        115                 120                 125

Leu Thr Ser Val Glu Thr Val Gln Pro Ala Ser Thr Glu Val Glu Thr
    130                 135                 140

Ser Gln Pro Thr Pro Met Glu Ala Asp Thr Ser Lys Pro Ala Pro Met
145                 150                 155                 160

Glu Ala Glu Thr Ser Gln Pro Ala Pro Met Glu Ala Glu Thr Ser Gln
                165                 170                 175

Pro Ala Pro Met Glu Ala Glu Thr Ser Gln Pro Ala Pro Met Glu Ala
            180                 185                 190

Glu Thr Ser Gln Pro Ala Pro Asn Glu Ala Glu Thr Ser Lys Pro Ala
        195                 200                 205

Pro Thr Glu Ala Glu Thr Ser Lys Pro Ala Pro Thr Glu Ala Glu Thr
    210                 215                 220

Thr Gln Leu Pro Arg Ile Gln Ala Val Lys Thr Leu Phe Thr Thr Ser
225                 230                 235                 240

Ala Ala Thr Glu Val Pro Ser Thr Glu Pro Thr Thr Met Glu Thr Ala
                245                 250                 255

Ser Thr Glu Ser Asn Glu Ser Thr Ile Phe Leu Gly Pro Ser Val Thr
            260                 265                 270

His Leu Pro Asp Ser Gly Leu Lys Lys Gly Leu Ile Val Thr Pro Gly
        275                 280                 285

Ser Ser Pro Ala Pro Thr Leu Pro Gly Ser Ser Asp Leu Ile Pro Val
    290                 295                 300

Lys Gln Cys Leu Leu Ile Ile Leu Ile Leu Ala Ser Leu Ala Thr Ile
305                 310                 315                 320

Phe Leu Val Cys Thr Val Val Leu Ala Val Arg Leu Ser Arg Lys Thr
                325                 330                 335

His Met Tyr Pro Val Arg Asn Tyr Ser Pro Thr Glu Met Ile Cys Ile
            340                 345                 350

Ser Ser Leu Leu Pro Glu Gly Gly Asp Gly Ala Pro Val Thr Ala Asn
        355                 360                 365

Gly Gly Leu Pro Lys Val Gln Asp Leu Lys Thr Glu Pro Ser Gly Asp
    370                 375                 380

Arg Asp Gly Asp Asp Leu Thr Leu His Ser Phe Leu Pro
385                 390                 395
```

<210> SEQ ID NO 7
<211> LENGTH: 22
<212> TYPE: DNA
<213> ORGANISM: Artificial
<220> FEATURE:
<223> OTHER INFORMATION: PCR primer

<400> SEQUENCE: 7
gtgaagcagt gcctgctggc ca 22

<210> SEQ ID NO 8
<211> LENGTH: 32
<212> TYPE: DNA
<213> ORGANISM: Artificial
<220> FEATURE:
<223> OTHER INFORMATION: PCR primer

<400> SEQUENCE: 8

-continued

```
ctctcccgca agaaccacac acataccccg tg                                    32


<210> SEQ ID NO 9
<211> LENGTH: 23
<212> TYPE: DNA
<213> ORGANISM: Artificial
<220> FEATURE:
<223> OTHER INFORMATION: PCR primer

<400> SEQUENCE: 9

tggtttgcat ctcatccctg ctg                                              23


<210> SEQ ID NO 10
<211> LENGTH: 25
<212> TYPE: DNA
<213> ORGANISM: Artificial
<220> FEATURE:
<223> OTHER INFORMATION: PCR primer

<400> SEQUENCE: 10

caccatgttt ctgcaactcc tgctg                                            25


<210> SEQ ID NO 11
<211> LENGTH: 45
<212> TYPE: DNA
<213> ORGANISM: Artificial
<220> FEATURE:
<223> OTHER INFORMATION: PCR primer

<400> SEQUENCE: 11

ctaatacgca tcactatagg gcaagcagtg gtatcaacgc agagt                      45


<210> SEQ ID NO 12
<211> LENGTH: 45
<212> TYPE: DNA
<213> ORGANISM: Artificial
<220> FEATURE:
<223> OTHER INFORMATION: PCR primer

<400> SEQUENCE: 12

ctaatacgac tcactatagg gccgtagctg cgggttgggt ggtca                      45


<210> SEQ ID NO 13
<211> LENGTH: 26
<212> TYPE: DNA
<213> ORGANISM: Artificial
<220> FEATURE:
<223> OTHER INFORMATION: PCR primer

<400> SEQUENCE: 13

agggaggaag ctgtgcaggg tgaggt                                           26


<210> SEQ ID NO 14
<211> LENGTH: 26
<212> TYPE: DNA
<213> ORGANISM: Artificial
<220> FEATURE:
<223> OTHER INFORMATION: PCR primer

<400> SEQUENCE: 14

gaaagggagg aagctgtgca gggtga                                           26


<210> SEQ ID NO 15
<211> LENGTH: 10
<212> TYPE: PRT
<213> ORGANISM: Equine
```

-continued

<220> FEATURE:
<221> NAME/KEY: MISC_FEATURE
<222> LOCATION: (1)..(1)
<223> OTHER INFORMATION: N at position 1 can be Ala or Leu
<220> FEATURE:
<221> NAME/KEY: MISC_FEATURE
<222> LOCATION: (10)..(10)
<223> OTHER INFORMATION: N at position 10 can be Val, Arg, Ala, or Lys

<400> SEQUENCE: 15

```
Asn Thr Glu Ala Leu Ser Thr Glu Pro Asn
1               5                   10
```

<210> SEQ ID NO 16
<211> LENGTH: 31
<212> TYPE: PRT
<213> ORGANISM: Equine
<220> FEATURE:
<221> NAME/KEY: hPSGL-1_PL1_mAb-binding_epitope
<222> LOCATION: (15)..(28)

<400> SEQUENCE: 16

```
Gln Leu Val Arg Gly Gln Thr Gly Val Ser Lys Tyr Leu His Arg Asp
1               5                   10                  15

Asp Val Asn Arg Glu Gly Thr Asp Leu Leu Lys Thr Pro Glu Ser
            20                  25                  30
```

<210> SEQ ID NO 17
<211> LENGTH: 42
<212> TYPE: PRT
<213> ORGANISM: Bovine
<220> FEATURE:
<221> NAME/KEY: hPSGL-1_PL1_mAb-binding_epitope
<222> LOCATION: (29)..(42)

<400> SEQUENCE: 17

```
Gln Leu Gly Glu Thr Ser Thr Asn Glu Thr Val Lys Ala Pro Gly Pro
1               5                   10                  15

Leu Tyr Pro Gly Glu Glu Arg Asp Pro Glu Asp Asp Glu Asp Tyr Asp
            20                  25                  30

Tyr Ile Gly Gln Thr Asp Pro Pro Glu Met
        35                  40
```

<210> SEQ ID NO 18
<211> LENGTH: 21
<212> TYPE: PRT
<213> ORGANISM: Human
<220> FEATURE:
<221> NAME/KEY: hPSGL-1_PL1_mAb-binding_epitope
<222> LOCATION: (8)..(21)

<400> SEQUENCE: 18

```
Gln Ala Thr Glu Tyr Glu Tyr Leu Asp Tyr Asp Phe Leu Pro Glu Thr
1               5                   10                  15

Glu Pro Pro Glu Met
            20
```

<210> SEQ ID NO 19
<211> LENGTH: 22
<212> TYPE: PRT
<213> ORGANISM: Murine
<220> FEATURE:
<221> NAME/KEY: hPSGL-1_PL1_mAb-binding_epitope
<222> LOCATION: (9)..(22)

<400> SEQUENCE: 19

-continued

```
Gln Val Val Gly Asp Asp Asp Phe Glu Asp Pro Asp Tyr Thr Tyr Asn
1               5                   10                  15

Thr Asp Pro Pro Glu Met
            20
```